US008530624B2

(12) United States Patent
Roberts et al.

(10) Patent No.: US 8,530,624 B2
(45) **Date of Patent: *Sep. 10, 2013**

(54) OSTEOPROTEGERIN VARIANT PROTEINS

(75) Inventors: Anthony Roberts, North Fitzroy (AU); George Kopsidas, Preston (AU); Gregory Coia, Brunswick (AU); Merilyn Sleigh, Neutral Bay (AU); Vincent Batori, Preston (AU)

(73) Assignee: Cephalon Australia (VIC) Pty Ltd, Macquarie Park (AU)

(*) Notice: Subject to any disclaimer, the term of this patent is extended or adjusted under 35 U.S.C. 154(b) by 357 days.

This patent is subject to a terminal disclaimer.

(21) Appl. No.: 12/584,802

(22) Filed: Sep. 11, 2009

(65) Prior Publication Data

US 2010/0144600 A1 Jun. 10, 2010

Related U.S. Application Data

(63) Continuation of application No. 11/303,169, filed on Dec. 13, 2005, now Pat. No. 7,612,169.

(60) Provisional application No. 60/635,722, filed on Dec. 13, 2004.

(51) Int. Cl.

| | |
|---|---|
| *C07K 14/00* | (2006.01) |
| *C07K 14/435* | (2006.01) |
| *C07K 14/46* | (2006.01) |
| *C07K 14/47* | (2006.01) |
| *C07K 14/475* | (2006.01) |

(52) U.S. Cl.
USPC .......................................................... 530/350

(58) Field of Classification Search
None
See application file for complete search history.

(56) References Cited

U.S. PATENT DOCUMENTS

| | | | |
|---|---|---|---|
| 5,350,836 | A | 9/1994 | Kopchick et al. |
| 6,015,938 | A | 1/2000 | Boyle et al. |
| 6,087,555 | A | 7/2000 | Dunstan et al. |
| 6,284,728 | B1 | 9/2001 | Boyle et al. |
| 6,284,740 | B1 | 9/2001 | Boyle et al. |
| 6,288,032 | B1 | 9/2001 | Boyle et al. |
| 6,316,408 | B1 | 11/2001 | Boyle et al. |
| 6,369,027 | B1 | 4/2002 | Boyle et al. |
| 6,613,644 | B2 | 9/2003 | Lachner |
| 7,612,169 | B2 | 11/2009 | Roberts et al. |
| 2003/0207827 | A1 | 11/2003 | Boyle |
| 2003/0219864 | A1 | 11/2003 | Desjarlais |

FOREIGN PATENT DOCUMENTS

| | | | |
|---|---|---|---|
| WO | WO 97/23614 | A1 | 7/1997 |
| WO | WO 98/49305 | | 11/1998 |
| WO | WO 99/58661 | A1 | 11/1999 |
| WO | WO 01/03719 | A2 | 1/2001 |
| WO | WO 01/17543 | A2 | 3/2001 |
| WO | WO 01/18203 | A1 | 3/2001 |
| WO | WO 01/44472 | A1 | 6/2001 |
| WO | WO 02/064782 | A2 | 8/2002 |
| WO | WO 03/084560 | A2 | 10/2003 |
| WO | WO 2004/039995 | A1 | 5/2004 |

OTHER PUBLICATIONS

Wells (1990) Biochemistry, 29:8509-8517.
Ngo et al. (1994) The protein folding problem and tertiary structure prediction, Merz et al., eds., Birkhauser, Boston, pp. 491-495.
Theoleyre et al. (2004) "The molecular triad OPG/RANK/RANKL: involvement in the orchestration of pathophysiological bone remodeling," *Cytokine & Growth Factor Reviews*, 15(6): 457-475.
Yonou et al. 2003 "Osteoprotegerin/osteoclastogenesis inhibitory factor decreases human prostate cancer burden in human adult bone implanted into nonobese diabetic/severe combined immunodeficient mice," *Cancer Research*, 63(9):2096-2102.
Adler et al., (2002) "Immunotherapy as a Means to Induce Transplantation Tolerance." *Current Opinion in Immunology*, 14: 660-665.
Anderson et al. (1997) "A Homologue of the TNF Receptor and its Ligand Enhance T-Cell Growth and Dendritic-Cell Function." *Nature*, 390(6656): 175-179.
Atkins et al., (2001) "Osteoprotegerin Inhibits Osteoclast Formation and Bone Resorbing Activity in Giant Cell Tumors of Bone." *Bone*, 28: 370-437.
Bekker et al., (2001) "The Effect of a Single Dose of Osteoprotegerin in Postmenopausal Women." *Journal of Bone Mineral Research*, 16: 348-60.
Body et al., (2003) "A Phase I Study of AMGN-007, a Recombinant Osteoprotegerin Construct, in Patients with Multiple Myeloma or Breast Carcinoma Related Bone Metastases." *Cancer*, 97: 887-92.

Bolon et al., (2002) "Duration of Bone Protection by a Single Osteoprotegerin Injection in Rats with Adjuvant-Induced Arthritis." Cellular and Molecular Life Sciences, 59: 1569-1576.

Cheng et al., (2003) "Disabling of Receptor Activator of Nuclear Factor-kB (RANK) Receptor Complex by Novel Osteoprotegerin-Like Peptidomimetics Restores Bone Loss in Vivo," *The Journal of Biological Chemistry*, 279: 8269-8277.
Coia et al., (1996)"Construction of Recombinant Extended Single-Chain Antibody Peptide Conjugates for Use in the Diagnosis of HIV-1 and HIV-2," *Journal of Immunological Methods*, 192: 13-23.

(Continued)

*Primary Examiner* — Elizabeth C Kemmerer
(74) *Attorney, Agent, or Firm* — Quine Intellectual Property Law Group, P.C.

(57) ABSTRACT

The present invention relates to novel osteoprotegerin variant proteins (GYPs) that demonstrate reduced binding affinity for their ligand TRAIL when compared to wild-type osteoprotegerin. Nucleic acids which encode these GYPs are also provided. Recombinant vectors and host cells expressing these GYPs are also encompassed as are methods of producing recombinant GYPs. The present invention also relates to compositions comprising these GYPs, and to methods of treating bone diseases characterised by increased bone turnover and/or loss. The GYPs of the invention are useful for preventing bone resorption and may be used to treat any condition resulting in abnormal bone turnover or bone loss such as osteoporosis, hypercalcemia, Paget's disease of bone, multiple myeloma, bone cancer and bone loss due to rheumatoid arthritis or osteomyelitis, and the like.

21 Claims, 16 Drawing Sheets

(56) References Cited

OTHER PUBLICATIONS

Cross et al. (2005) "Osteoprotegerin (OPG)—A Potential New Role in the Regulation of Endothelialcell Phonotype and Tumour Angiogenesis" *International Journal of Cancer,*, Nov. 14, 2005 (epub).

Croucher et al. (2001) "Osteoprotegerin Inhibits the Development of Osteolytic Bone Disease in Multiple Myeloma," *Blood*, 98: 3524-3540.

Daroszewska et al. (2004) "Susceptibility to Paget's Disease of Bone is Influenced by a Common Polymorphic Variant of Osteoprotegerin," *Journal of Bone and Mineral Research*,. 19: 1506-11.

Doran et al. (2004) "Native Osteoprotegerin Gene Transfer Inhibits the Development of Murine Osteolyt ic Bone Disease Induced by Tumor Xenografts." *Experimental. Hematorlogy*, 32: 351-59.

Emery et al. (1998) "Osteoprotegerin is a Receptor for the Cytotoxic Ligand TRAIL," *The Journal of Biological Chemistry*, 273: 14363-14367.

Gardnerova et al. (2000) "The Use of TNF Family Ligands and Receptors and Agents Which Modify Their Interaction as Therapeutic Agents," *Current Drug Targets*, 1: 327-364.

Guiliani et al., (2004) "New Insight in the Mechanism of Osteoclast Activation and Formation in Mulitple Myeloma: Focus on the Receptor Activator of NF-kB Ligand (FRANKL)," *Experimental Hematology*, 32: 685-691.

He et al. (2004) "Structure of Nerve Growth Factor Complexed with the Shared Neurotrophin Receptor." *Science*, 304: 870-875.

Hofbauer et al. (2001) "Receptor Activator of Nuclear Factor-kB Ligand and Osteoprotegerin." *Cancer Research*, 92(3): 460-470.

Hofbauer et al. (2004) "Clinical Implications of the Osteoprotegerin/RANKL/RANK System for Bone and Vascular Diseases," *Journal of the American Medical Association*, 292:490-495.

Holen et al. (2002) "Osteoprotegerin (OPG) is a Survival Factor for Human Prostate Cancer Cells," *Cancer Research*, 62: 1619-1623.

Honore et al. (2000) "Osteoprotegerin Block Bone Cancer-Induced Skeletal Destructions, Skeletal Pain and Pain-Related Neurochemical Reorganiztion of the Spinal Cord," *Nature Medicine*, 6(5): 521-528.

Hsu et al. (1999) "Tumor Necrosis Factor Receptor Family Member RANK Mediates Osteoclast Differentiation and activation Induced by Osteoprotegerin Ligand," *Proceedings of the National Academy of Sciences*, USA, 96: 3540-3545.

Hymowitz et al. (1999) "Triggering Cell Death: The Crystal Structure of Apo2l/TRAIL in a Complex with Death Receptor 5," *Molecular Cell*, 4: 563-571.

Igney et al. (2002) "Death and Anti-Death: Tumour Resistance to Apoptosis," *Nature, Reviews/Cancer*, 2: 277-288.

Ito et al. (2002) "Crystal Structure of the Extracellular Domain of Mouse RANK Ligand at 2.2-Å Resolution," *Journal of Biological Chemistry*, 277: 6631-6636.

Kaden et al. (2004) "Unbalanced RANKL/RANK Pathway in Aortic Valve Sclerosis," *Journal of Moecular and Cellular Cardiology*, 36: 17-19.

Kong et al. (1999) "OPGL is a Key Regulator of Osteoclastogenesis, Lymphocyte Development and Lymph-Node Organogenesis," *Nature*, 397: 315-323.

Kostenuik et al. (2001) "OPG and PTH-(1-34) Have Additive Effects on Bone Density and Mechanical Strength in Osteopenic Ovariectomized Rats," *Endoncrinology*, 142: 4295-4304.

Lacey et al. (2000) "Osteoprotegerin Ligand Modulates Murine Osteoclast Survival in Vitro and in Vivo," *American Journal of Pathology*, 157: 435-448.

Lacey et al. (1998) "Osteoprotegerin Ligand is a Cytokine that Regulates Osteoclast Differentiation and Activation," *Cell*, 93: 165-176.

Liu et al. (2004) "Production of Recombinant Human Osteoprotegerin From Trichoplusia NI Cells and Bornbyx Mori Larvae," *Protein and Peptide Letters* 11: 317-323.

Lorenz et al., (2004) "Clinical Implications of the Osteoprotegerin/RANKL/RANK System for Bone and Vascular Diseases." *Journal of the American Medical Association*, 292: 490-495.

Luger et al. (2001) "Osteoprotegerin Diminishes Advanced Bone Cancer Pain," *Cancer Research*, 61: 4038-4047.

Mitsiades et al. (2002) "Activation of NF-KB and Upregulation of Intracellular Anti-Apoptotic Proteins Via the IGF-1/Akt Signaling in Human Multiple Myeloma Cells: Therapeutic Implications," *Oncogene*, 21: 5673-5683.

Mongkolsapaya et al., (1999) "Structure of the TRAIL-DR5 Complex Reveals Mechanisms Conferring Specificity in Apoptotic Initiation," *Nature Structural Biology*, 6: 1048-1053.

Morony et al., (1999) "A Chimeric Form of Osteoprotegerin Inhibits Hypercalcemia and Bone Resorption Induced by II-1$^\beta$, TNF$_\alpha$, PTH, PTHrP, and 1,25 (OH)$_2$D$_3$," *Journal of Bone and Mineral Research*, 14: 1478-1485.

Mundy et al. (2002) "Metastasis to Bone: Causes, Consequences and Therapeutic Opportunities," *Nature Reviews Cancer*, 2: 584-593.

Neville-Webbe et al., (2004) "Osteoprotegerin (OPG) Produced by Bone Marrow Stromal Cells Protects Breast Cancer Cells From TRAIL-Induced Apoptosis," *Breast Cancer Research and Treatment*, 86: 269-279.

Oyajobi et al., (2000) "Therapeutic Efficacy of a Soluble Receptor Activator of Nuclear Factor kB-IgG Fc Fusion Protein in Suppressing Bone Resorption and Hypercalcemia in a Model of Humoral Hypercalcemia of Malignancy," *Cancer Res.*, 61(6): 521-528.

Pearse et al. (2001) Multiple Myeloma Disrupts the TRANCE/Osteoprotegerin Cytokine Axis to Trigger Bone Destruction and Promote Tumor Progression, *Proceedings of the National Academy of Sciences*, USA, 98(2): 11581-11586.

Roux and Marriete, (2004) "The High Rate of Bone Resorption in Multiple Myeloma is Due to RANK (Receptor Activator of Nuclear Factor-kB) and RANK Ligand Expression," *Leukemia & Lymphoma*, 45: 1111-1118.

Schneeweis et al., (2005) "Functional Dissection of Osteoprotegerin and Its Interaction with Receptor Activator of NF-kB Ligand," *Journal of Biological Chemistry*, 280(5): 41155-41164.

Shipman and Croucher, (2003) "Osteoprotegerin is a Soluable Decoy Receptor for Tumor Necrosis Factor-Related Apoptosis-Inducing Ligand/Apo2 Ligand and Can Function as a Paracrine Survival Factor for Human Myeloma Cells," *Cancer Research*, 63: 912-916.

Simon et al., (1992) "Peptoids: A Modular Approach to Drug Discovery," *Proceedings of the National Academy of Sciences*, USA, 89(20): 9367-9371.

Simonet et al., (1997) "Osteoprotegerin: A Novel Secreted Protein Involved in the Regulation of Bone Density," *Cell*, 89: 309-319.

Soufi et al., (2004) "Osteoprotegerin Gene Polymorphisms in Men with Coronary Artery Disease," *The Journal of Clinical Endocrinololgy & Metabolism*, 89: 3764-3768.

Terpos et al., (2003) "Soluble Receptor Activator of Nuclear Factor kB Ligand-Osteoprotegerin Ratio Predicts Survival in Multiple Myeloma: Proposal for a Novel Prognostic Index," *Blood*, 102: 1064-1069.

Tomoyasu et al., (1998) "Characterization of Monomeric and Homodimeric Forms of Osteoclastogenesis Inhibitory Factor," *Biochemical and Biophysical Research Communications*, 245: 382-387.

Truneh et al., (2000) "Temperature-Sensitive Differential Affinity of TRAIL for Its Receptors," *The Journal of Biological Chemistry*, 275(30): 23319-23325.

Vanderkerken et al., (2003) "Multiple Myeloma Biology: Lessons from the 5TMM Models," *Immunological Reviews*, 194: 196-206.

Willard et al., (2000) "Expression, Purification, and Characterization of the Human Receptor-Activator of NF-kB Ligand (RANKL) Extracellular Domain," *Protein Expression and Purification*, 20: 48-57.

Yamaguchi et al., (1998) "Characterization of Structural Domains of Human Osteoclastogenesis Inhibitory Factor." *Journal of Biological Chemistry*, 273: 5117-5123.

Yasuda et al. (1998) "Identity of Osteoclastogenesis Inhibitory Factor (OCIF) and Osteoprotegerin (OPG): A Mechanism by Which OPG/OCIF Inhibits Osteoclastogenesis in Vitro." *Endocrinology*, 139: 1329-1337.

```
RNTVCKRCPDGFFSNETSSKAPCRKHTNCSVFGLLLTQKGNATHDNICSGNSESTQK    OPGwt   (SEQ ID NO:5)
..........................................................  OVP1R34 (SEQ ID NO:6)
..........................................................  OVP1R17 (SEQ ID NO:7)
..........................................................  OVP2R32 (SEQ ID NO:8)
..........................................................  OVP2R39 (SEQ ID NO:9)
..........................................................  OVP2T7  (SEQ ID NO:10)
......................D...................................  OVP2T39 (SEQ ID NO:11)
..........................................................  OVP2eR36 (SEQ ID NO:12)
................................G.........................  OVP1R34QR30 (SEQ ID NO:13)
..........................................................  OVP1R34QT42 (SEQ ID NO:14)
......................A...................................  OVPT13  (SEQ ID NO:19)
..........................................................  OVPR4   (SEQ ID NO:50)
.D........................................................  OVPR23b (SEQ ID NO:20)
..........................................................  OVPR12c (SEQ ID NO:51)

Decoration 'Decoration #1': Box residues that differ from OPGwt.seq.
Decoration 'Decoration #2': Hide (as '.') residues that match OPGwt.seq exactly.
```

Fig. 8 Cont.

SEQUENCE LISTING

<160> NUMBER OF SEQ ID NOS: 49

<210> SEQ ID NO 1
<211> LENGTH: 2291
<212> TYPE: DNA
<213> ORGANISM: Human
<220> FEATURE:
<221> NAME/KEY: CDS
<222> LOCATION: (252)..(1454)

<400> SEQUENCE: 1

```
ctttccgccc cagccctgaa agcgttaacc ctggagcttt ctgcacaccc cccgaccgct      60
cccgcccaag cttcctaaaa aagaaaggtg caaagtttgg tccaggatag aaaaatgact     120
gatcaaaggc aggcgatact tcctgttgcc gggacgctat atataacgtg atgagcgcac     180
gggctgcgga gacgcaccgg agcgctcgcc cagccgccgc ctccaagccc ctgaggtttc     240
cggggaccac a atg aac aag ttg ctg tgc tgc gcg ctc gtg ttt ctg gac      290
          Met Asn Lys Leu Leu Cys Cys Ala Leu Val Phe Leu Asp
            1               5                  10 atc tcc att aag tgg acc acc cag gaa acg ttt cct cca aag tac ctt       338
Ile Ser Ile Lys Trp Thr Thr Gln Glu Thr Phe Pro Pro Lys Tyr Leu
     15                  20                  25 cat tat gac gaa gaa acc tct cat cag ctg ttg tgt gac aaa tgt cct       386
His Tyr Asp Glu Glu Thr Ser His Gln Leu Leu Cys Asp Lys Cys Pro
 30                  35                  40                  45 cct ggt acc tac cta aaa caa cac tgt aca gca aag tgg aag acc gtg       434
Pro Gly Thr Tyr Leu Lys Gln His Cys Thr Ala Lys Trp Lys Thr Val
                 50                  55                  60
```

| | | |
|---|---|---|
| tgc gcc cct tgc cct gac cac tac tac aca gac agc tgg cac acc agt<br>Cys Ala Pro Cys Pro Asp His Tyr Tyr Thr Asp Ser Trp His Thr Ser<br>          65                        70                        75 | 482 |
| gac gag tgt cta tac tgc agc ccc gtg tgc aag gag ctg cag tac gtc<br>Asp Glu Cys Leu Tyr Cys Ser Pro Val Cys Lys Glu Leu Gln Tyr Val<br>          80                        85                        90 | 530 |
| aag cag gag tgc aat cgc acc cac aac cgc gtg tgc gaa tgc aag gaa<br>Lys Gln Glu Cys Asn Arg Thr His Asn Arg Val Cys Glu Cys Lys Glu<br>95                        100                       105 | 578 |
| ggg cgc tac ctt gag ata gag ttc tgc ttg aaa cat agg agc tgc cct<br>Gly Arg Tyr Leu Glu Ile Glu Phe Cys Leu Lys His Arg Ser Cys Pro<br>110                   115                   120                   125 | 626 |
| cct gga ttt gga gtg gtg caa gct gga acc cca gag cga aat aca gtt<br>Pro Gly Phe Gly Val Val Gln Ala Gly Thr Pro Glu Arg Asn Thr Val<br>                        130                       135                   140 | 674 |
| tgc aaa aga tgt cca gat ggg ttc ttc tca aat gag acg tca tct aaa<br>Cys Lys Arg Cys Pro Asp Gly Phe Phe Ser Asn Glu Thr Ser Ser Lys<br>               145                       150                   155 | 722 |
| gca ccc tgt aga aaa cac aca aat tgc agt gtc ttt ggt ctc ctg cta<br>Ala Pro Cys Arg Lys His Thr Asn Cys Ser Val Phe Gly Leu Leu Leu<br>        160                       165                       170 | 770 |
| act cag aaa gga aat gca aca cac gac aac ata tgt tcc gga aac agt<br>Thr Gln Lys Gly Asn Ala Thr His Asp Asn Ile Cys Ser Gly Asn Ser<br>        175                       180                       185 | 818 |
| gaa tca act caa aaa tgt gga ata gat gtt acc ctg tgt gag gag gca<br>Glu Ser Thr Gln Lys Cys Gly Ile Asp Val Thr Leu Cys Glu Glu Ala<br>190                       195                       200                   205 | 866 |
| ttc ttc agg ttt gct gtt cct aca aag ttt acg cct aac tgg ctt agt<br>Phe Phe Arg Phe Ala Val Pro Thr Lys Phe Thr Pro Asn Trp Leu Ser<br>                    210                       215                   220 | 914 |
| gtc ttg gta gac aat ttg cct ggc acc aaa gta aac gca gag agt gta<br>Val Leu Val Asp Asn Leu Pro Gly Thr Lys Val Asn Ala Glu Ser Val<br>                        225                       230                   235 | 962 |
| gag agg ata aaa cgg caa cac agc tca caa gaa cag act ttc cag ctg<br>Glu Arg Ile Lys Arg Gln His Ser Ser Gln Glu Gln Thr Phe Gln Leu<br>        240                       245                       250 | 1010 |
| ctg aag tta tgg aaa cat caa aac aaa gac caa gat ata gtc aag aag<br>Leu Lys Leu Trp Lys His Gln Asn Lys Asp Gln Asp Ile Val Lys Lys<br>255                       260                       265 | 1058 |
| atc atc caa gat att gac ctc tgt gaa aac agc gtg cag cgg cac att<br>Ile Ile Gln Asp Ile Asp Leu Cys Glu Asn Ser Val Gln Arg His Ile<br>270                       275                       280                   285 | 1106 |
| gga cat gct aac ctc acc ttc gag cag ctt cgt agc ttg atg gaa agc<br>Gly His Ala Asn Leu Thr Phe Glu Gln Leu Arg Ser Leu Met Glu Ser<br>                    290                       295                   300 | 1154 |
| tta ccg gga aag aaa gtg gga gca gaa gac att gaa aaa aca ata aag<br>Leu Pro Gly Lys Lys Val Gly Ala Glu Asp Ile Glu Lys Thr Ile Lys<br>                    305                       310                   315 | 1202 |
| gca tgc aaa ccc agt gac cag atc ctg aag ctg ctc agt ttg tgg cga<br>Ala Cys Lys Pro Ser Asp Gln Ile Leu Lys Leu Leu Ser Leu Trp Arg<br>        320                       325                       330 | 1250 |
| ata aaa aat ggc gac caa gac acc ttg aag ggc cta atg cac gca cta<br>Ile Lys Asn Gly Asp Gln Asp Thr Leu Lys Gly Leu Met His Ala Leu<br>        335                       340                       345 | 1298 |
| aag cac tca aag acg tac cac ttt ccc aaa act gtc act cag agt cta<br>Lys His Ser Lys Thr Tyr His Phe Pro Lys Thr Val Thr Gln Ser Leu<br>350                       355                       360                   365 | 1346 |
| aag aag acc atc agg ttc ctt cac agc ttc aca atg tac aaa ttg tat<br>Lys Lys Thr Ile Arg Phe Leu His Ser Phe Thr Met Tyr Lys Leu Tyr<br>                    370                       375                   380 | 1394 |

```
cag aag tta ttt tta gaa atg ata ggt aac cag gtc caa tca gta aaa    1442
Gln Lys Leu Phe Leu Glu Met Ile Gly Asn Gln Val Gln Ser Val Lys
            385                 390                 395 ata agc tgc tta taactggaaa tggccattga gctgtttcct cacaattggc         1494
Ile Ser Cys Leu
        400 gagatcccat ggatgagtaa actgtttctc aggcacttga ggctttcagt gatatctttc   1554 tcattaccag tgactaattt tgccacaggg tactaaaaga aactatgatg tggagaaagg   1614 actaacatct cctccaataa accccaaatg gttaatccaa ctgtcagatc tggatcgtta   1674 tctactgact atattttccc ttattactgc ttgcagtaat tcaactggaa attaaaaaaa   1734 aaaaactaga ctccattgtg ccttactaaa tatgggaatg tctaacttaa atagctttga   1794 gatttcagct atgctagagg cttttattag aaagccatat tttttttctgt aaaagttact  1854 aatatatctg taacactatt acagtattgc tatttatatt cattcagata taagatttgt   1914 acatattatc atcctataaa gaaacggtat gacttaattt tagaaagaaa attatattct   1974 gtttattatg acaaatgaaa gagaaaatat atattttaa tggaaagttt gtagcatttt    2034 tctaataggt actgccatat ttttctgtgt ggagtatttt taaattttta tctgtataag   2094 ctgtaatatc attttataga aaatgcatta tttagtcaat tgtttaatgt tggaaaacat   2154 atgaaatata aattatctga atattagatg ctctgagaaa ttgaatgtac cttatttaaa   2214 agatttatg gttttataac tatataaatg acattattaa agttttcaaa ttattttta    2274 aaaaaaaaaa aaaaaaa                                                   2291

<210> SEQ ID NO 2
<211> LENGTH: 401
<212> TYPE: PRT
<213> ORGANISM: Human

<400> SEQUENCE: 2

Met Asn Lys Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Thr Gln Lys
                165                 170                 175

Gly Asn Ala Thr His Asp Asn Ile Cys Ser Gly Asn Ser Glu Ser Thr
            180                 185                 190
```

-continued

```
Gln Lys Cys Gly Ile Asp Val Thr Leu Cys Glu Glu Ala Phe Phe Arg
    195                 200                 205

Phe Ala Val Pro Thr Lys Phe Thr Pro Asn Trp Leu Ser Val Leu Val
210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
    290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
            340                 345                 350

Lys Thr Tyr His Phe Pro Lys Thr Val Thr Gln Ser Leu Lys Lys Thr
        355                 360                 365

Ile Arg Phe Leu His Ser Phe Thr Met Tyr Lys Leu Tyr Gln Lys Leu
    370                 375                 380

Phe Leu Glu Met Ile Gly Asn Gln Val Gln Ser Val Lys Ile Ser Cys
385                 390                 395                 400

Leu

<210> SEQ ID NO 3
<211> LENGTH: 401
<212> TYPE: PRT
<213> ORGANISM: Rat

<400> SEQUENCE: 3

Met Asn Lys Trp Leu Cys Cys Ala Leu Leu Val Phe Leu Asp Ile Ile
1               5                   10                  15

Glu Trp Thr Thr Gln Glu Thr Phe Pro Pro Lys Tyr Leu His Tyr Asp
            20                  25                  30

Pro Glu Thr Gly Arg Gln Leu Leu Cys Asp Lys Cys Ala Pro Gly Thr
        35                  40                  45

Tyr Leu Lys Gln His Cys Thr Val Arg Arg Lys Thr Leu Cys Val Pro
    50                  55                  60

Cys Pro Asp Tyr Ser Tyr Thr Asp Ser Trp His Thr Ser Asp Glu Cys
65                  70                  75                  80

Val Tyr Cys Ser Pro Val Cys Lys Glu Leu Gln Thr Val Lys Gln Glu
                85                  90                  95

Cys Asn Arg Thr His Asn Arg Val Cys Glu Cys Glu Glu Gly Arg Tyr
            100                 105                 110

Leu Glu Leu Glu Phe Cys Leu Lys His Arg Ser Cys Pro Pro Gly Leu
        115                 120                 125

Gly Val Leu Gln Ala Gly Thr Pro Glu Arg Asn Thr Val Cys Lys Arg
    130                 135                 140

Cys Pro Asp Gly Phe Phe Ser Gly Glu Thr Ser Ser Lys Ala Pro Cys
145                 150                 155                 160

Arg Lys His Thr Asn Cys Ser Ser Leu Gly Leu Leu Leu Ile Gln Lys
```

```
                165                 170                 175
Gly Asn Ala Thr His Asp Asn Val Cys Ser Gly Asn Arg Glu Ala Thr
            180                 185                 190

Gln Asn Cys Gly Ile Asp Val Thr Leu Cys Glu Glu Ala Phe Phe Arg
        195                 200                 205

Phe Ala Val Pro Thr Lys Ile Ile Pro Asn Trp Leu Ser Val Leu Val
210                 215                 220

Asp Ser Leu Pro Gly Thr Lys Val Asn Ala Glu Ser Val Glu Arg Ile
225                 230                 235                 240

Lys Arg Arg His Ser Ser Gln Glu Gln Thr Phe Gln Leu Leu Lys Leu
                245                 250                 255

Trp Lys His Gln Asn Arg Asp Gln Glu Met Val Lys Lys Ile Ile Gln
            260                 265                 270

Asp Ile Asp Leu Cys Glu Ser Ser Val Gln Arg His Ile Gly His Ala
        275                 280                 285

Asn Leu Thr Thr Glu Gln Leu Arg Ile Leu Met Glu Ser Leu Pro Gly
    290                 295                 300

Lys Lys Ile Ser Pro Asp Glu Ile Glu Arg Thr Arg Lys Thr Cys Lys
305                 310                 315                 320

Pro Ser Glu Gln Leu Leu Lys Leu Leu Ser Leu Trp Arg Ile Lys Asn
                325                 330                 335

Gly Asp Gln Asp Thr Leu Lys Gly Leu Met Tyr Ala Leu Lys His Leu
            340                 345                 350

Lys Ala Tyr His Phe Pro Lys Thr Val Thr His Ser Leu Arg Lys Thr
        355                 360                 365

Ile Arg Phe Leu His Ser Phe Thr Met Tyr Arg Leu Tyr Gln Lys Leu
    370                 375                 380

Phe Leu Glu Met Ile Gly Asn Gln Val Gln Ser Val Lys Ile Ser Cys
385                 390                 395                 400

Leu

<210> SEQ ID NO 4
<211> LENGTH: 401
<212> TYPE: PRT
<213> ORGANISM: Mouse

<400> SEQUENCE: 4

Met Asn Lys Trp Leu Cys Cys Ala Leu Leu Val Leu Asp Ile Ile
1               5                   10                  15

Glu Trp Thr Thr Gln Glu Thr Leu Pro Pro Lys Tyr Leu His Tyr Asp
                20                  25                  30

Pro Glu Thr Gly His Gln Leu Leu Cys Asp Lys Cys Ala Pro Gly Thr
            35                  40                  45

Tyr Leu Lys Gln His Cys Thr Val Arg Arg Lys Thr Leu Cys Val Pro
    50                  55                  60

Cys Pro Asp His Ser Tyr Thr Asp Ser Trp His Thr Ser Asp Glu Cys
65                  70                  75                  80

Val Tyr Cys Ser Pro Val Cys Lys Glu Leu Gln Ser Val Lys Gln Glu
                85                  90                  95

Cys Asn Arg Thr His Asn Arg Val Cys Glu Cys Glu Glu Gly Arg Tyr
            100                 105                 110

Leu Glu Ile Glu Phe Cys Leu Lys His Arg Ser Cys Pro Pro Gly Ser
    115                 120                 125

Gly Val Val Gln Ala Gly Thr Pro Glu Pro Asn Thr Val Cys Lys Lys
130                 135                 140
```

```
Cys Pro Asp Gly Phe Phe Ser Gly Glu Thr Ser Ser Lys Ala Pro Cys
145                 150                 155                 160

Arg Lys His Thr Asp Cys Ser Thr Phe Gly Leu Leu Ile Gln Lys
            165                 170                 175

Gly Asn Ala Thr His Asp Asn Val Cys Ser Gly Asn Arg Glu Ala Thr
            180                 185                 190

Gln Lys Cys Gly Ile Asp Val Thr Leu Cys Glu Glu Ala Phe Phe Arg
            195                 200                 205

Phe Ala Val Pro Thr Lys Ile Ile Pro Asn Trp Leu Ser Val Leu Val
            210                 215                 220

Asp Ser Leu Pro Gly Thr Lys Val Asn Ala Glu Ser Val Glu Arg Ile
225                 230                 235                 240

Lys Arg Arg His Ser Ser Gln Glu Gln Thr Phe Gln Leu Leu Lys Leu
                245                 250                 255

Trp Lys His Gln Asn Arg Asp Gln Glu Met Val Lys Lys Ile Ile Gln
                260                 265                 270

Asp Ile Asp Leu Cys Glu Ser Ser Val Gln Arg His Leu Gly His Ala
            275                 280                 285

Asn Leu Thr Thr Glu Gln Leu Arg Ala Leu Met Glu Ser Leu Pro Gly
            290                 295                 300

Lys Lys Ile Ser Pro Glu Glu Ile Glu Arg Thr Arg Lys Thr Cys Lys
305                 310                 315                 320

Ser Ser Glu Gln Leu Leu Lys Leu Leu Ser Leu Trp Arg Ile Lys Asn
                325                 330                 335

Gly Asp Gln Asp Thr Leu Lys Gly Leu Met Tyr Ala Leu Lys His Leu
                340                 345                 350

Lys Thr Ser His Phe Pro Lys Thr Val Thr His Ser Leu Arg Lys Thr
            355                 360                 365

Met Arg Phe Leu His Ser Phe Thr Met Tyr Arg Leu Tyr Gln Lys Leu
            370                 375                 380

Phe Leu Glu Met Ile Gly Asn Gln Val Gln Ser Val Lys Ile Ser Cys
385                 390                 395                 400

Leu

<210> SEQ ID NO 5
<211> LENGTH: 173
<212> TYPE: PRT
<213> ORGANISM: Artificial
<220> FEATURE:
<223> OTHER INFORMATION: Human variant protein

<400> SEQUENCE: 5

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
        50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Ile Glu Phe
                85                  90                  95

Cys Leu Lys His Arg Ser Cys Pro Pro Gly Phe Gly Val Val Gln Ala
```

```
            100                 105                 110
Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 6
<211> LENGTH: 173
<212> TYPE: PRT
<213> ORGANISM: Artificial
<220> FEATURE:
<223> OTHER INFORMATION: Human variant protein

<400> SEQUENCE: 6

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Arg Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Thr Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 7
<211> LENGTH: 173
<212> TYPE: PRT
<213> ORGANISM: Artificial
<220> FEATURE:
<223> OTHER INFORMATION: Human variant protein

<400> SEQUENCE: 7

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
```

-continued

```
                65                  70                  75                  80
Asn Arg Val Cys Glu Cys Lys Glu Gly Arg Tyr Leu Glu Met Glu Phe
                    85                  90                  95

Cys Leu Lys His Arg Ser Cys Pro Pro Gly Phe Gly Val Val Gln Ala
                100                 105                 110

Gly Thr Pro Glu Arg Asn Thr Val Cys Lys Arg Cys Pro Asp Gly Phe
            115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 8
<211> LENGTH: 173
<212> TYPE: PRT
<213> ORGANISM: Artificial
<220> FEATURE:
<223> OTHER INFORMATION: Human variant protein

<400> SEQUENCE: 8

Glu Thr Phe Pro Pro Lys Tyr Leu His Asp Asp Glu Glu Thr Ser His
1               5                   10                  15

Gln Leu Leu Cys Asp Lys Cys Pro Pro Gly Thr Tyr Leu Lys Gln His
                20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Ile Glu Phe
                    85                  90                  95

Cys Leu Lys His Arg Ser Cys Pro Pro Gly Phe Gly Glu Val Gln Ala
                100                 105                 110

Gly Thr Pro Glu Arg Asn Thr Val Cys Lys Arg Cys Pro Asp Gly Phe
            115                 120                 125

Phe Ser Asn Glu Thr Ser Ser Lys Ala Pro Cys Arg Lys His Thr Asn
    130                 135                 140

Cys Ser Asp Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 9
<211> LENGTH: 173
<212> TYPE: PRT
<213> ORGANISM: Artificial
<220> FEATURE:
<223> OTHER INFORMATION: Human variant protein

<400> SEQUENCE: 9

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
                20                  25                  30

Cys Thr Ala Lys Trp Lys Thr Val Cys Ala Pro Cys Pro Asp His Tyr
```

```
                 35                  40                  45
Tyr Thr Asp Ser Trp His Thr Ser Asp Glu Cys Leu Tyr Cys Ser Pro
             50                  55                  60
Val Cys Lys Glu Leu Gln Tyr Val Lys Gln Glu Cys Asn Arg Thr His
 65                  70                  75                  80
Asn Arg Val Cys Glu Cys Lys Glu Gly Arg Tyr Leu Glu Ile Glu Phe
                 85                  90                  95
Cys Leu Lys His Gly Ser Cys Pro Pro Gly Phe Gly Val Val Gln Ala
            100                 105                 110
Gly Thr Pro Glu Arg Asn Thr Val Cys Lys Arg Cys Pro Asp Gly Phe
            115                 120                 125
Phe Ser Asn Glu Thr Ser Ser Lys Ala Pro Cys Arg Lys His Thr Asn
130                 135                 140
Cys Ser Val Phe Gly Leu Leu Leu Thr Gln Lys Gly Asn Ala Thr His
145                 150                 155                 160
Asp Asn Ile Cys Ser Gly Asn Ser Glu Ser Thr Gln Lys
                165                 170

<210> SEQ ID NO 10
<211> LENGTH: 173
<212> TYPE: PRT
<213> ORGANISM: Artificial
<220> FEATURE:
<223> OTHER INFORMATION: Human variant protein

<400> SEQUENCE: 10

Glu Thr Phe Pro Pro Lys Tyr Leu His Tyr Asp Glu Glu Thr Ser His
 1               5                  10                  15
Gln Leu Leu Cys Asp Lys Cys Pro Pro Gly Thr Tyr Leu Lys Gln His
                20                  25                  30
Cys Thr Ala Lys Trp Lys Thr Val Cys Ala Pro Cys Pro Asp His Tyr
             35                  40                  45
Tyr Thr Asp Ser Trp His Thr Ser Asp Glu Cys Leu Tyr Cys Ser Pro
             50                  55                  60
Val Cys Lys Glu Leu Gln Tyr Val Lys Gln Glu Cys Asn Arg Thr His
 65                  70                  75                  80
Asn Arg Val Cys Glu Cys Lys Glu Gly Arg Tyr Leu Glu Thr Glu Phe
                 85                  90                  95
Cys Leu Lys His Arg Ser Cys Pro Pro Gly Val Gly Val Val Gln Ala
            100                 105                 110
Gly Thr Pro Glu Arg Asn Thr Val Cys Lys Arg Cys Pro Asp Gly Phe
            115                 120                 125
Phe Ser Asn Glu Thr Ser Ser Lys Ala Pro Cys Arg Lys His Thr Asn
130                 135                 140
Cys Ser Val Phe Gly Leu Leu Leu Thr Gln Lys Gly Asn Ala Thr His
145                 150                 155                 160
Asp Asn Ile Cys Ser Gly Asn Ser Glu Ser Thr Gln Lys
                165                 170

<210> SEQ ID NO 11
<211> LENGTH: 173
<212> TYPE: PRT
<213> ORGANISM: Artificial
<220> FEATURE:
<223> OTHER INFORMATION: Human variant protein

<400> SEQUENCE: 11

Glu Thr Phe Pro Pro Lys Tyr Leu His Tyr Asp Glu Glu Thr Ser His
```

```
                1               5                  10                 15
Gln Leu Leu Cys Asp Lys Cys Pro Pro Gly Thr Tyr Leu Lys Gln His
                    20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
        50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Val Glu Phe
                85                  90                  95

Cys Leu Lys His Arg Ser Cys Pro Pro Gly Phe Gly Val Val Gln Ala
                    100                 105                 110

Gly Thr Pro Glu Arg Asn Thr Val Cys Lys Arg Cys Pro Asp Gly Phe
                115                 120                 125

Phe Ser Asn Glu Thr Ser Ser Lys Ala Pro Cys Arg Lys His Thr Asn
            130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 12
<211> LENGTH: 173
<212> TYPE: PRT
<213> ORGANISM: Artificial
<220> FEATURE:
<223> OTHER INFORMATION: Human variant protein

<400> SEQUENCE: 12

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
                    20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
        50                  55                  60

Val Cys Lys Glu Leu Gln Tyr Val Lys Gln Glu Cys Asn Arg Thr His
65                  70                  75                  80

Asp Arg Val Cys Glu Cys Lys Glu Gly Arg Tyr Leu Glu Ile Glu Phe
                85                  90                  95

Cys Leu Lys His Arg Ser Cys Pro Pro Gly Phe Gly Val Val Gln Ala
                    100                 105                 110

Gly Thr Pro Glu Arg Asn Thr Val Cys Lys Arg Cys Pro Asp Gly Phe
                115                 120                 125

Phe Ser Asn Glu Thr Ser Ser Lys Ala Pro Cys Arg Lys His Thr Asn
            130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 13
<211> LENGTH: 173
<212> TYPE: PRT
<213> ORGANISM: Artificial
```

```
<220> FEATURE:
<223> OTHER INFORMATION: Human variant protein

<400> SEQUENCE: 13

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Arg Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Thr Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Gly Val Phe Gly Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 14
<211> LENGTH: 173
<212> TYPE: PRT
<213> ORGANISM: Artificial
<220> FEATURE:
<223> OTHER INFORMATION: Human variant protein

<400> SEQUENCE: 14

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Arg Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly His Tyr Leu Glu Thr Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170
```

<210> SEQ ID NO 15
<211> LENGTH: 173
<212> TYPE: PRT
<213> ORGANISM: Artificial
<220> FEATURE:
<223> OTHER INFORMATION: Human variant protein

<400> SEQUENCE: 15

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
                20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
        50                  55                  60

Val Cys Lys Glu Leu Gln Tyr Val Lys Gln Glu Cys Asp Arg Thr His
65                  70                  75                  80

Asn Arg Val Cys Glu Cys Lys Glu Gly Arg Tyr Leu Glu Ile Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 16
<211> LENGTH: 173
<212> TYPE: PRT
<213> ORGANISM: Artificial
<220> FEATURE:
<223> OTHER INFORMATION: Human variant protein

<400> SEQUENCE: 16

Glu Thr Phe Pro Pro Lys Tyr Leu His Tyr Asp Glu Glu Ala Ser His
1               5                   10                  15

Gln Leu Leu Cys Asp Lys Cys Pro Pro Gly Thr Tyr Leu Lys Gln His
                20                  25                  30

Cys Thr Ala Lys Trp Lys Thr Val Cys Ala Pro Cys Pro Asp His Tyr
            35                  40                  45

Tyr Ala Asp Ser Trp His Thr Ser Asp Glu Cys Leu Tyr Cys Ser Pro
        50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Ile Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

```
Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
            165                 170
```

<210> SEQ ID NO 17
<211> LENGTH: 173
<212> TYPE: PRT
<213> ORGANISM: Artificial
<220> FEATURE:
<223> OTHER INFORMATION: Human variant protein

<400> SEQUENCE: 17

```
Glu Thr Phe Pro Pro Lys Tyr Leu His Tyr Asp Glu Thr Ser His
1               5                   10                  15

Gln Leu Leu Cys Asp Lys Cys Pro Pro Gly Thr Tyr Leu Lys Gln His
                20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Ile Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Thr Ser Lys Ala Pro Cys Arg Lys His Thr Asn
130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
            165                 170
```

<210> SEQ ID NO 18
<211> LENGTH: 173
<212> TYPE: PRT
<213> ORGANISM: Artificial
<220> FEATURE:
<223> OTHER INFORMATION: Human variant protein

<400> SEQUENCE: 18

```
Glu Thr Phe Pro Pro Lys Tyr Leu His Tyr Asp Glu Thr Ser His
1               5                   10                  15

Gln Gln Leu Cys Asp Lys Cys Pro Pro Gly Thr Tyr Leu Lys Gln His
                20                  25                  30

Cys Thr Ala Glu Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Ile Glu Phe
                85                  90                  95

Cys Leu Lys His Arg Ser Cys Pro Pro Gly Phe Gly Val Val Gln Ala
            100                 105                 110
```

```
Gly Thr Pro Glu Arg Asn Thr Val Cys Lys Arg Cys Pro Asp Gly Phe
            115                 120                 125

Phe Ser Asn Glu Thr Ser Ser Lys Ala Pro Cys Arg Lys His Thr Asn
        130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 19
<211> LENGTH: 173
<212> TYPE: PRT
<213> ORGANISM: Artificial
<220> FEATURE:
<223> OTHER INFORMATION: Human variant protein

<400> SEQUENCE: 19

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Met Glu Phe
                85                  90                  95

Cys Leu Lys His Arg Ser Cys Pro Pro Gly Phe Gly Val Val Gln Ala
            100                 105                 110

Gly Thr Pro Glu Arg Asp Thr Val Cys Arg Cys Pro Asp Gly Phe
            115                 120                 125

Phe Ser Asn Glu Thr Ser Ser Lys Ala Pro Cys Arg Lys His Thr Asn
        130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 20
<211> LENGTH: 173
<212> TYPE: PRT
<213> ORGANISM: Artificial
<220> FEATURE:
<223> OTHER INFORMATION: Human variant protein

<400> SEQUENCE: 20

Glu Thr Phe Pro Pro Lys Tyr Leu His Tyr Asp Glu Glu Thr Ser His
1               5                   10                  15

Gln Leu Ser Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80
```

```
Asn Arg Val Cys Glu Cys Lys Glu Gly Arg Tyr Leu Glu Met Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170
```

<210> SEQ ID NO 21
<211> LENGTH: 173
<212> TYPE: PRT
<213> ORGANISM: Artificial
<220> FEATURE:
<223> OTHER INFORMATION: Human variant protein

<400> SEQUENCE: 21

```
Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Leu Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170
```

<210> SEQ ID NO 22
<211> LENGTH: 173
<212> TYPE: PRT
<213> ORGANISM: Artificial
<220> FEATURE:
<223> OTHER INFORMATION: Human variant protein

<400> SEQUENCE: 22

```
Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
        35                  40                  45
```

```
Tyr Thr Asp Ser Trp His Thr Ser Asp Glu Cys Leu Tyr Cys Ser Pro
         50                  55                  60

Val Cys Lys Glu Leu Gln Tyr Val Lys Gln Glu Cys Asn Arg Thr His
 65                  70                  75                  80

Asn Arg Val Cys Glu Cys Lys Glu Gly Arg Tyr Leu Glu Trp Glu Phe
                 85                  90                  95

Cys Leu Lys His Arg Ser Cys Pro Pro Gly Phe Gly Val Val Gln Ala
                100                 105                 110

Gly Thr Pro Glu Arg Asn Thr Val Cys Lys Arg Cys Pro Asp Gly Phe
            115                 120                 125

Phe Ser Asn Glu Thr Ser Ser Lys Ala Pro Cys Arg Lys His Thr Asn
130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170
```

<210> SEQ ID NO 23
<211> LENGTH: 173
<212> TYPE: PRT
<213> ORGANISM: Artificial
<220> FEATURE:
<223> OTHER INFORMATION: Human variant protein

<400> SEQUENCE: 23

```
Glu Thr Phe Pro Pro Lys Tyr Leu His Tyr Asp Glu Glu Thr Ser His
 1               5                  10                  15

Gln Leu Leu Cys Asp Lys Cys Pro Pro Gly Thr Tyr Leu Lys Gln His
                 20                  25                  30

Cys Thr Ala Lys Trp Lys Thr Val Cys Ala Pro Cys Pro Asp His Tyr
             35                  40                  45

Tyr Thr Asp Ser Trp His Thr Ser Asp Glu Cys Leu Tyr Cys Ser Pro
         50                  55                  60

Val Cys Lys Glu Leu Gln Tyr Val Lys Gln Glu Cys Asn Arg Thr His
 65                  70                  75                  80

Asn Arg Val Cys Glu Cys Lys Glu Gly Arg Tyr Leu Glu Phe Glu Phe
                 85                  90                  95

Cys Leu Lys His Arg Ser Cys Pro Pro Gly Phe Gly Val Val Gln Ala
                100                 105                 110

Gly Thr Pro Glu Arg Asn Thr Val Cys Lys Arg Cys Pro Asp Gly Phe
            115                 120                 125

Phe Ser Asn Glu Thr Ser Ser Lys Ala Pro Cys Arg Lys His Thr Asn
130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170
```

<210> SEQ ID NO 24
<211> LENGTH: 173
<212> TYPE: PRT
<213> ORGANISM: Artificial
<220> FEATURE:
<223> OTHER INFORMATION: Human variant protein

<400> SEQUENCE: 24

```
Glu Thr Phe Pro Pro Lys Tyr Leu His Tyr Asp Glu Glu Thr Ser His
 1               5                  10                  15
```

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
 50                  55                  60

Val Cys Lys Glu Leu Gln Tyr Val Lys Gln Glu Cys Asn Arg Thr His
 65                  70                  75                  80

Asn Arg Val Cys Glu Cys Lys Glu Gly Arg Tyr Leu Glu Ala Glu Phe
                85                  90                  95

Cys Leu Lys His Arg Ser Cys Pro Pro Gly Phe Gly Val Val Gln Ala
                100                 105                 110

Gly Thr Pro Glu Arg Asn Thr Val Cys Lys Arg Cys Pro Asp Gly Phe
                115                 120                 125

Phe Ser Asn Glu Thr Ser Ser Lys Ala Pro Cys Arg Lys His Thr Asn
            130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 25
<211> LENGTH: 173
<212> TYPE: PRT
<213> ORGANISM: Artificial
<220> FEATURE:
<223> OTHER INFORMATION: Human variant protein

<400> SEQUENCE: 25

Glu Thr Phe Pro Pro Lys Tyr Leu His Tyr Asp Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
 50                  55                  60

Val Cys Lys Glu Leu Gln Tyr Val Lys Gln Glu Cys Asn Arg Thr His
 65                  70                  75                  80

Asn Arg Val Cys Glu Cys Lys Glu Gly Arg Tyr Leu Glu Gly Glu Phe
                85                  90                  95

Cys Leu Lys His Arg Ser Cys Pro Pro Gly Phe Gly Val Val Gln Ala
                100                 105                 110

Gly Thr Pro Glu Arg Asn Thr Val Cys Lys Arg Cys Pro Asp Gly Phe
                115                 120                 125

Phe Ser Asn Glu Thr Ser Ser Lys Ala Pro Cys Arg Lys His Thr Asn
            130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 26
<211> LENGTH: 173
<212> TYPE: PRT
<213> ORGANISM: Artificial
<220> FEATURE:

<223> OTHER INFORMATION: Human variant protein

<400> SEQUENCE: 26

| Glu | Thr | Phe | Pro | Pro | Lys | Tyr | Leu | His | Tyr | Asp | Glu | Glu | Thr | Ser | His |
|---|---|---|---|---|---|---|---|---|---|---|---|---|---|---|---|
| 1 | | | | 5 | | | | | 10 | | | | | 15 | |

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Pro Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 27
<211> LENGTH: 173
<212> TYPE: PRT
<213> ORGANISM: Artificial
<220> FEATURE:
<223> OTHER INFORMATION: Human variant protein

<400> SEQUENCE: 27

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Asn Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 28
<211> LENGTH: 173
<212> TYPE: PRT
<213> ORGANISM: Artificial
<220> FEATURE:
<223> OTHER INFORMATION: Human variant protein

<400> SEQUENCE: 28

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Gln Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 29
<211> LENGTH: 173
<212> TYPE: PRT
<213> ORGANISM: Artificial
<220> FEATURE:
<223> OTHER INFORMATION: Human variant protein

<400> SEQUENCE: 29

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Ser Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

```
Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170
```

<210> SEQ ID NO 30
<211> LENGTH: 173
<212> TYPE: PRT
<213> ORGANISM: Artificial
<220> FEATURE:
<223> OTHER INFORMATION: Human variant protein

<400> SEQUENCE: 30

```
Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
                20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Arg Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170
```

<210> SEQ ID NO 31
<211> LENGTH: 173
<212> TYPE: PRT
<213> ORGANISM: Artificial
<220> FEATURE:
<223> OTHER INFORMATION: Human variant protein

<400> SEQUENCE: 31

```
Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
                20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Lys Glu Phe
                85                  90                  95

Cys Leu Lys His Arg Ser Cys Pro Pro Gly Phe Gly Val Val Gln Ala
            100                 105                 110
```

```
Gly Thr Pro Glu Arg Asn Thr Val Cys Lys Arg Cys Pro Asp Gly Phe
            115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 32
<211> LENGTH: 173
<212> TYPE: PRT
<213> ORGANISM: Artificial
<220> FEATURE:
<223> OTHER INFORMATION: Human variant protein

<400> SEQUENCE: 32

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Tyr Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
            115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 33
<211> LENGTH: 173
<212> TYPE: PRT
<213> ORGANISM: Artificial
<220> FEATURE:
<223> OTHER INFORMATION: Human variant protein

<400> SEQUENCE: 33

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80
```

```
Asn Arg Val Cys Glu Cys Lys Glu Gly Arg Tyr Leu Glu Asp Glu Phe
            85                   90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
            115                 120                 125

Phe Ser Asn Glu Thr Ser Ser Lys Ala Pro Cys Arg Lys His Thr Asn
            130                 135             140

Cys Ser Val Phe Gly Leu Leu Leu Thr Gln Lys Gly Asn Ala Thr His
145             150                 155                 160

Asp Asn Ile Cys Ser Gly Asn Ser Glu Ser Thr Gln Lys
            165                 170
```

<210> SEQ ID NO 34
<211> LENGTH: 173
<212> TYPE: PRT
<213> ORGANISM: Artificial
<220> FEATURE:
<223> OTHER INFORMATION: Human variant protein

<400> SEQUENCE: 34

```
Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
50              55                  60

Val Cys Lys Glu Leu Gln Tyr Val Lys Gln Glu Cys Asn Arg Thr His
65              70                  75                  80

Asn Arg Val Cys Glu Cys Lys Glu Gly Arg Tyr Leu Glu Glu Glu Phe
            85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
            115                 120                 125

Phe Ser Asn Glu Thr Ser Ser Lys Ala Pro Cys Arg Lys His Thr Asn
            130                 135             140

Cys Ser Val Phe Gly Leu Leu Leu Thr Gln Lys Gly Asn Ala Thr His
145             150                 155                 160

Asp Asn Ile Cys Ser Gly Asn Ser Glu Ser Thr Gln Lys
            165                 170
```

<210> SEQ ID NO 35
<211> LENGTH: 173
<212> TYPE: PRT
<213> ORGANISM: Artificial
<220> FEATURE:
<223> OTHER INFORMATION: Human variant protein

<400> SEQUENCE: 35

```
Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
            35                  40                  45
```

```
Tyr Thr Asp Ser Trp His Thr Ser Asp Glu Cys Leu Tyr Cys Ser Pro
 50                  55                  60

Val Cys Lys Glu Leu Gln Tyr Val Lys Gln Glu Cys Asn Arg Thr His
 65                  70                  75                  80

Asn Arg Val Cys Glu Cys Lys Glu Gly Arg Tyr Leu Glu Met Glu Phe
                 85                  90                  95

Cys Leu Lys His Gly Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 36
<211> LENGTH: 173
<212> TYPE: PRT
<213> ORGANISM: Artificial
<220> FEATURE:
<223> OTHER INFORMATION: Human variant protein

<400> SEQUENCE: 36

Glu Thr Phe Pro Pro Lys Tyr Leu His Tyr Asp Glu Glu Thr Ser His
 1               5                  10                  15

Gln Leu Leu Cys Asp Lys Cys Pro Pro Gly Thr Tyr Leu Lys Gln His
                 20                  25                  30

Cys Thr Ala Lys Trp Lys Thr Val Cys Ala Pro Cys Pro Asp His Tyr
             35                  40                  45

Tyr Thr Asp Ser Trp His Thr Ser Asp Glu Cys Leu Tyr Cys Ser Pro
 50                  55                  60

Val Cys Lys Glu Leu Gln Tyr Val Lys Gln Glu Cys Asn Arg Thr His
 65                  70                  75                  80

Asn Arg Val Cys Glu Cys Lys Glu Gly Arg Tyr Leu Glu Met Glu Phe
                 85                  90                  95

Cys Leu Lys His Asn Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 37
<211> LENGTH: 173
<212> TYPE: PRT
<213> ORGANISM: Artificial
<220> FEATURE:
<223> OTHER INFORMATION: Human variant protein

<400> SEQUENCE: 37

Glu Thr Phe Pro Pro Lys Tyr Leu His Tyr Asp Glu Glu Thr Ser His
 1               5                  10                  15
```

```
Gln Leu Leu Cys Asp Lys Cys Pro Gly Thr Tyr Leu Lys Gln His
        20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Met Glu Phe
                85                  90                  95

Cys Leu Lys His Gln Ser Cys Pro Pro Gly Phe Gly Val Val Gln Ala
                100                 105                 110

Gly Thr Pro Glu Arg Asn Thr Val Cys Lys Arg Cys Pro Asp Gly Phe
            115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 38
<211> LENGTH: 173
<212> TYPE: PRT
<213> ORGANISM: Artificial
<220> FEATURE:
<223> OTHER INFORMATION: Human variant protein

<400> SEQUENCE: 38

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
        20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Met Glu Phe
                85                  90                  95

Cys Leu Lys His Ser Ser Cys Pro Pro Gly Phe Gly Val Val Gln Ala
                100                 105                 110

Gly Thr Pro Glu Arg Asn Thr Val Cys Lys Arg Cys Pro Asp Gly Phe
            115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 39
<211> LENGTH: 173
<212> TYPE: PRT
<213> ORGANISM: Artificial
<220> FEATURE:
<223> OTHER INFORMATION: Human variant protein
```

-continued

```
<400> SEQUENCE: 39

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Met Glu Phe
                85                  90                  95

Cys Leu Lys His Asp Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 40
<211> LENGTH: 173
<212> TYPE: PRT
<213> ORGANISM: Artificial
<220> FEATURE:
<223> OTHER INFORMATION: Human variant protein

<400> SEQUENCE: 40

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Met Glu Phe
                85                  90                  95

Cys Leu Lys His Glu Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170
```

```
<210> SEQ ID NO 41
<211> LENGTH: 173
<212> TYPE: PRT
<213> ORGANISM: Artificial
<220> FEATURE:
<223> OTHER INFORMATION: Human variant protein

<400> SEQUENCE: 41

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Met Glu Phe
                85                  90                  95

Cys Leu Lys His Arg Ser Cys Pro Pro Gly Leu Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 42
<211> LENGTH: 173
<212> TYPE: PRT
<213> ORGANISM: Artificial
<220> FEATURE:
<223> OTHER INFORMATION: Human variant protein

<400> SEQUENCE: 42

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Met Glu Phe
                85                  90                  95

Cys Leu Lys His Arg Ser Cys Pro Pro Gly Ala Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Thr Gln Lys Gly Asn Ala Thr His
```

```
                145                 150                 155                 160
Asp Asn Ile Cys Ser Gly Asn Ser Glu Ser Thr Gln Lys
                    165                 170

<210> SEQ ID NO 43
<211> LENGTH: 173
<212> TYPE: PRT
<213> ORGANISM: Artificial
<220> FEATURE:
<223> OTHER INFORMATION: Human variant protein

<400> SEQUENCE: 43

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
                20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
        50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Met Glu Phe
                85                  90                  95

Cys Leu Lys His Arg Ser Cys Pro Pro Gly Pro Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                    165                 170

<210> SEQ ID NO 44
<211> LENGTH: 173
<212> TYPE: PRT
<213> ORGANISM: Artificial
<220> FEATURE:
<223> OTHER INFORMATION: Human variant protein

<400> SEQUENCE: 44

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
                20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
        50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Met Glu Phe
                85                  90                  95

Cys Leu Lys His Arg Ser Cys Pro Pro Gly Ser Gly Val Val Gln Ala
            100                 105                 110

Gly Thr Pro Glu Arg Asn Thr Val Cys Lys Arg Cys Pro Asp Gly Phe
```

```
                    115                 120                 125
Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 45
<211> LENGTH: 173
<212> TYPE: PRT
<213> ORGANISM: Artificial
<220> FEATURE:
<223> OTHER INFORMATION: Human variant protein

<400> SEQUENCE: 45

Glu Thr Phe Pro Pro Lys Tyr Leu His Tyr Asp Glu Thr Ser His
1               5                   10                  15

Gln Leu Leu Cys Asp Lys Cys Pro Pro Gly Thr Tyr Leu Lys Gln His
                20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
        50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Met Glu Phe
                85                  90                  95

Cys Leu Lys His Arg Ser Cys Pro Pro Gly Thr Gly Val Val Gln Ala
                100                 105                 110

Gly Thr Pro Glu Arg Asn Thr Val Cys Lys Arg Cys Pro Asp Gly Phe
            115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys
                165                 170

<210> SEQ ID NO 46
<211> LENGTH: 173
<212> TYPE: PRT
<213> ORGANISM: Artificial
<220> FEATURE:
<223> OTHER INFORMATION: Human variant protein

<400> SEQUENCE: 46

Glu Thr Phe Pro Pro Lys Tyr Leu His Tyr Asp Glu Thr Ser His
1               5                   10                  15

Gln Leu Leu Cys Asp Lys Cys Pro Pro Gly Thr Tyr Leu Lys Gln His
                20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
        50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Met Glu Phe
```

```
                    85                  90                  95
Cys Leu Lys His Arg Ser Cys Pro Pro Gly Ile Gly Val Val Gln Ala
            100                 105                 110
Gly Thr Pro Glu Arg Asn Thr Val Cys Lys Arg Cys Pro Asp Gly Phe
            115                 120                 125
Phe Ser Asn Glu Thr Ser Ser Lys Ala Pro Cys Arg Lys His Thr Asn
            130                 135                 140
Cys Ser Val Phe Gly Leu Leu Thr Gln Lys Gly Asn Ala Thr His
145                 150                 155                 160
Asp Asn Ile Cys Ser Gly Asn Ser Glu Ser Thr Gln Lys
                165                 170

<210> SEQ ID NO 47
<211> LENGTH: 173
<212> TYPE: PRT
<213> ORGANISM: Artificial
<220> FEATURE:
<223> OTHER INFORMATION: Human variant protein

<400> SEQUENCE: 47

Glu Thr Phe Pro Pro Lys Tyr Leu His Tyr Asp Glu Glu Thr Ser His
1               5                   10                  15
Gln Leu Ser Cys Asp Lys Cys Pro Pro Gly Thr Tyr Leu Lys Gln His
            20                  25                  30
Cys Thr Ala Lys Trp Lys Thr Val Cys Ala Pro Cys Pro Asp His Tyr
            35                  40                  45
Tyr Thr Asp Ser Trp His Thr Ser Asp Glu Cys Leu Tyr Cys Ser Pro
        50                  55                  60
Val Cys Lys Glu Leu Gln Tyr Val Lys Gln Glu Cys Asn Arg Thr His
65                  70                  75                  80
Asn Arg Val Cys Glu Cys Lys Glu Gly His Tyr Leu Glu Met Glu Phe
                85                  90                  95
Cys Leu Lys His Arg Ser Cys Pro Pro Gly Phe Gly Val Val Gln Ala
            100                 105                 110
Gly Thr Pro Glu Arg Asn Thr Val Cys Lys Arg Cys Pro Asp Gly Phe
            115                 120                 125
Phe Ser Asn Glu Thr Ser Ser Lys Ala Pro Cys Arg Lys His Thr Asn
            130                 135                 140
Cys Ser Val Phe Gly Leu Leu Leu Thr Gln Lys Gly Asn Ala Thr His
145                 150                 155                 160
Asp Asn Ile Cys Ser Gly Asn Ser Glu Ser Thr Gln Lys
                165                 170

<210> SEQ ID NO 48
<211> LENGTH: 51
<212> TYPE: DNA
<213> ORGANISM: Primer

<400> SEQUENCE: 48
tattactcgc ggcccagccg gccatgaaca agttgctgtg ctgcgcgctc g        51

<210> SEQ ID NO 49
<211> LENGTH: 50
<212> TYPE: DNA
<213> ORGANISM: Primer

<400> SEQUENCE: 49
catctttata atctgcggcc gctaagcagc ttattttac tgattggacc             50
```

OSTEOPROTEGERIN VARIANT PROTEINS

This application is a continuation of U.S. Ser. No. 11/303,169, filed Dec. 13, 2005, now U.S. Pat. No. 7,612,169, entitled "OSTEOPROTEGERIN VARIANT PROTEINS" by Anthony Roberts, et al., which claims benefit under 35 U.S.C. §119(e) of U.S. Provisional Patent Application Ser. No. 60/635,722, filed Dec. 13, 2004, which applications are incorporated herein by reference in their entirety.

FIELD OF THE INVENTION

The present invention relates to evolved proteins that are useful in the regulation of biological effects mediated through the interaction of RANK and RANKL. More particularly, the invention relates to novel osteoprotegerin variant proteins (OVPs) that have altered binding specificities when compared to wild-type osteoprotegerin. Nucleic acids which encode these OVPs are also provided. Recombinant vectors and host cells expressing these OVPs are also encompassed as are methods of producing recombinant OVPs. The present invention also relates to compositions comprising these OVPs, and to methods of treating diseases associated with the a biological effect mediated through the interaction of RANK and RANKL.

BACKGROUND OF THE INVENTION

The Rank ligand (RANKL)/OPG/RANK biochemical axis has been successfully targeted to treat osteoporosis, rheumatoid arthritis, cancer-induced bone destruction, metastasis, hypercalcemia, and pain (Hofbauer et al., Cancer 92(3): p. 460-470 (2001). Therapies utilizing OPG (Honore et al., Nature Medicine 6(5):521-528 (2000)), an antibody directed to RANKL, or the soluble RANK-Fc protein (Oyajobi et al., Cancer Res 61(6): p. 2572-8 (2001)) are also in development. OPG and soluble RANK-Fc protein constructs bind to RANKL, thereby decreasing amount of RANKL that is available for RANK receptor activation.

In addition to being important in bone biology, RANKL plays a role in the immune system by regulating antigen-specific T cell responses (Anderson et al., Nature 390(6656): 175-9 (1997)). RANKL is highly expressed on activated T cells while the RANK receptor is expressed at high levels on mature dendritic cells (DC). The interaction between RANKL and RANK acts as a costimulatory signal, which enhances DC survival and T cell proliferation by inducing DC differentiation, cytokine production and reduced apoptosis in both cell types. Immunotherapy to produce tolerance to transplanted tissues and/or organs can be achieved by blocking the costimulatory signal using RANK antagonists. Blocking costimulation prevents T cell activation by DCs, and causes alloreactive T cells to become anergic and/or undergo apoptosis (Adler et al., Current Opinion in Immunology 14:660-665 (2002)). By a similar mechanism of action, antagonizing RANK signaling could be a treatment for autoimmune and immune-mediated inflammatory disorders such as systemic lupus erythematosus, inflammatory bowel disease, diabetes, multiple sclerosis, rheumatoid arthritis, and ankylosing spondylitis.

Osteoprotegerin (OPG) is a protein of the Tumour Necrosis Factor (TNF) receptor family, and was first described by Simonet et al. (Cell, 89, 309-319 (1997)).

OPG appears to be a crucial element in regulating the natural processes of bone production and turnover. Changes in the balance between OPG and its target receptor RANKL have been noted in a number of conditions associated with abnormal bone metabolism.

OPG has undergone preclinical and clinical testing with potential for application in various conditions associated with increased bone turnover and bone loss, including osteoporosis, rheumatoid arthritis, Paget's disease, periodontal disease, vascular disease and cancers that are located in or have metastasised to bone (For review, see Lorenz et al., J. Amer Med Assoc 292: 490-5 (2004) and references therein). Extensive animal testing of OPG is reported in the literature, indicating equal or superior performance compared with other therapies currently used for reducing bone loss (Simonet et al., Cell, 89, 309-319 (1997); Bolon et al., Cell Mol Life Sci 59, 1569-76 (2002)). OPG has also been shown to reduce pain associated with bone cancers (Luger et al., Cancer Research 61, 4038-4047 (2001)).

OPG is described in detail in U.S. Pat. No. 6,015,938, U.S. Pat. No. 6,284,740, U.S. Pat. No. 6,284,728, U.S. Pat. No. 6,613,544, U.S. Pat. No. 6,316,408, U.S. Pat. No. 6,288,032 and U.S. Pat. No. 6,369,027. Transgenic mice lacking expression of OPG are described in U.S. Pat. No. 6,087,555.

OPG has undergone Phase I trials in both multiple myeloma patients and in osteoporosis patients for reduction of bone turnover. In preliminary Phase I/II studies in postmenopausal women suffering from osteoporosis, a single injection of OPG was found to suppress markers of bone turnover by 30-80% for several days (Bekker et al., J. Bone Miner Res 16, 348-360 (2001)). Multiple myeloma patients were treated with a range of doses of OPG, and showed up to 50% decrease in bone resorption over 30 or more days (Body et al., Cancer 97, 887-892 (2003)). Thus there is very strong evidence, both from preclinical studies and clinical studies, that OPG is likely to be a highly effective treatment in a variety of conditions characterised by abnormal bone metabolism.

The tumour necrosis factor (TNF) family of cytokines and their corresponding receptors contains a considerable number of members and there is substantial cross reactivity among members in ligand-receptor interactions (for review, see Igney, F. H. and Krammer, P. H Nature Reviews Cancer 2, 277-288 (2002)). TNF receptors generally trigger one of two kinds of response, either an apoptotic (programmed cell death) response or an effect on cell metabolic pathways via activation of the transcription factor NFkB. The receptor family also contains members which act as decoys, to reduce the effectiveness of interaction between other family ligand-receptor pairs. OPG appears to fall into this receptor class.

Compared with many TNF receptor family members, OPG is relatively restricted in its target specificity. According to current knowledge, OPG binds to only two TNF-like ligands:

1. RANKL (Receptor activator of NFkB ligand), a TNF-like cell surface molecule normally interacts with a TNF receptor family member, RANK, which is expressed on osteoclast precursors, dendritic cells T-cells and haematopoietic precursors (Kong et al., Nature 397:315-323 (1999). RANKL interacts with RANK on cell surfaces to stimulate the production and activity of osteoclasts, the principal cells involved in bone turnover (Hsu, H et al., Proc Natl Acad Sci USA 96, 3540-3545 (1999)). RANKL is expressed on stromal cells/osteoblasts (Kong et al., Nature 397:315-323 (1999)). The interaction of OPG with RANKL inhibits RANKL's ability to attach to RANK and stimulate osteoclasts and it is this activity of OPG that confers its ability to reduce bone loss (Lacey et al., Amer J Pathol 157, 435-448 (2000); Simonet et al., Cell, 89, 309-319 (1997)). The binding constant of dimeric OPG binding to RANKL has been reported as 6.7 nM (Willard et al., Protein Expr. Purif 20, 48-57 (2000)) with other reports placing the binding constant between 2 and 10 nM.

2. TRAIL (TNF-related apoptosis inducing ligand), a TNF-like cell surface molecule involved in the induction of apoptosis in cancer cells. OPG is seen as one of a small number of decoy receptors for TRAIL, acting to modulate its ability to target cancer cells (Reviewed in Igney and Krammer (2002) as referenced above). OPG would thus be expected to enhance cancer cell survival if present at a relevant site in sufficient quantities, and its ability to increase the survival of tumour cells has been documented (for example, Neville-Webbe et al., Breast Cancer Res Treat. 86, 271-82 (2004); Holen I et al., Cancer Res 62, 1619-1623 (2002)). The affinity of OPG for TRAIL has been reported as 3 nM (Emery et al., J. Biol. Chem. 273, 14363-7 (1998)) although this may vary with temperature (Truneh et al., J. Biol. Chem. 275, 23319-25 (2000)).

The ability of OPG to inhibit TRAIL activity, resulting in a possible increase in risk of cancer development, has been noted in the medical literature as a likely deterrent to the use of this agent as a therapeutic. Among the application areas for agents inhibiting bone loss are conditions such as osteoporosis and Paget's disease, which are not in themselves life threatening, but require long term therapy. Furthermore, one of the most important potential uses of OPG is in adjunct treatment of cancer patients with bone metastases. In all of these potential application areas, any indication of increased growth and survival of cancer cells associated with treatment would be a deterrent to use. Hence there is a need to generate a novel variant of OPG that substantially lacks TRAIL-binding capabilities. Such a variant would lack ability to significantly interfere with natural anti-cancer mechanisms while retaining its ability to interfere with the RANK/RANKL interaction that stimulates osteoclast formation and activity, and consequent bone loss.

SUMMARY OF THE INVENTION

The present inventors have now generated novel OPG Variant Proteins (OVPs) which demonstrate reduced binding affinity for TRAIL and reduced ability to inhibit the normal biological effects resulting from the interaction of TRAIL with its receptor.

Analysis of the OVPs of the present invention has revealed a focussing of point mutations in specific regions of the wild-type OPG protein sequence. In particular, the mutations are clustered in the region encompassed by OPG residues 102-130. Modelling studies conducted on the OVPs of the present invention support the idea that this region of OPG/OVP forms an interface with both TRAIL and RANKL proteins during binding. The identification of mutations within this region which can substantially alter the binding affinity for TRAIL without affecting attachment to RANKL is therefore surprising.

Importantly, the OVPs of the present invention retain the ability to bind to RANKL, and to reduce or inhibit the RANK-RANKL interaction and the consequent biological effects of this interaction. It is envisaged that preferred OVPs of the present invention will retain the ability of wild-type OPG to modulate bone metabolism, without having the undesired effect of enhancing survival of cancer cells through inhibition of the action of TRAIL.

Accordingly, the present invention provides an OPG variant protein comprising at least one modification when compared to wild-type OPG, wherein the OPG variant protein retains binding affinity for RANKL but exhibits reduced binding affinity for TRAIL when compared to wild-type OPG.

An OPG variant of the present invention includes any variant protein of OPG, whether truncated or full-length, in monomer or dimer form, which has significantly reduced attachment to TRAIL as a result of a modification to the protein, while substantially retaining its attachment to RANKL. Where comparisons are made between the activity of an OVP and that of wild type OPG, it will be appreciated that the comparison is made on the basis of proteins in a similar form with respect to size and dimerisation state.

In one preferred embodiment the OPG variant protein comprises at least one modification in the region encompassed by amino acid residues 102-130. For example, the OPG variant protein may comprise at least one amino acid substitution at position 102, 111, 115, 122, 128 or 130.

The present invention also provides an OVP protein which has been modified to induce dimerisation, or to maintain or improve its stability, expression or biological half life. Such modifications may include addition of an albumin moiety, an Fc region or substitution with polyethylene glycol, or addition of extensions which serve to maintain the OVP in a dimeric form.

The present invention also provides an isolated polynucleotide encoding an OPG variant protein of the present invention. Preferably, the polynucleotide is a variant of SEQ ID NO: 1, wherein the variant comprises nucleic acid changes such that it encodes the desired OPG variant protein of the invention. Methods of producing such nucleic acid changes are known in the art and are also described herein.

Variations on this sequence where the encoded protein maintains the same spectrum of biological activities are also provided. The nucleotide sequence may be altered to improve expression of the encoded protein in one or more expression systems, to increase RNA stability, or serendipitously, containing changes which do not diminish biological function of the nucleic acid or its encoded protein.

The present invention also provides a vector which comprises a polynucleotide according to the invention. Preferably, the vector is suitable for the replication and/or expression of a polynucleotide. The vectors may be, for example, a plasmid, virus or phage vector provided with an origin of replication, and preferably a promoter for the expression of the polynucleotide and optionally a regulator of the promoter. The vector may contain one or more selectable markers, for example an ampicillin resistance gene in the case of a bacterial plasmid or a neomycin resistance gene for a mammalian expression vector. The vector may be used in vitro, for example for the production of RNA or used to transfect or transform a host cell.

The present invention also provides a host cell which comprises a vector according to the invention, or contains the gene encoding one of the proteins of the invention under conditions that allow expression and production of the subject protein.

The present invention also provides a process for preparing an OPG variant protein of the invention, the process comprising cultivating a host cell of the invention under conditions which allow production of the OPG variant protein, and recovering the OPG variant protein. Such cells can be used for the production of commercially useful quantities of the encoded OPG variant protein.

The present invention also provides a method for reducing the binding affinity of OPG for TRAIL, the method comprising modifying at least one amino acid within an OPG protein or fragment thereof to produce an OPG variant protein, and testing the OPG variant protein for binding affinity for TRAIL.

In one preferred embodiment the method comprises modifying at least one amino acid within the region encompassed by residues 102-130 of wild type OPG to produce an OPG variant protein, and testing the OPG variant protein for binding affinity for TRAIL.

It will be appreciated that an OVP of the present invention can be used to reduce or inhibit the binding or RANK to RANKL in vivo, and reduce or inhibit the interaction between RANK and RANKL and the biological effects mediated through this interaction.

Accordingly, the present invention also provides a composition for inhibiting or reducing binding of RANK to RANKL, the composition comprising an OPG variant protein according to the invention, and one or more acceptable carriers.

The present invention also provides a pharmaceutical composition comprising a therapeutically effective amount of an OPG variant protein according to the invention and one or more of a pharmaceutically acceptable carrier, solubilizer, stabilizer and anti-oxidant.

The present invention also provides a method for inhibiting or reducing a biological effect mediated through the interaction of RANK and RANKL, the method comprising exposing a RANKL molecule to an OPG variant protein according to the present invention.

The present invention also provides a method for inhibiting or reducing a biological effect mediated through the interaction of RANK and RANKL in a subject, the method comprising administering to a subject an OPG variant protein according to the invention.

By "subject" herein is meant both humans and other animals, particularly mammals as outlined herein, with humans being preferred.

The present invention also provides a method for inhibiting or reducing differentiation, activation and/or survival of osteoclasts by RANKL, the method comprising exposing tissue containing osteoclasts or osteoclast precursor cells to an OPG variant protein according to the invention.

The present invention also provides a method for inhibiting or reducing differentiation, activation and/or survival of osteoclasts by RANKL in a subject, the method comprising administering to a subject an OPG variant protein according to the invention.

The present invention also provides method for preventing or treating a bone disorder comprising administering to a patient the pharmaceutical composition of the present invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The various features and embodiments of the present invention, referred to in individual sections herein, also apply as appropriate, to other sections. Consequently features specified in relation to one embodiment of the invention may be combined with features specified in relation to other embodiments, as appropriate.

KEY TO SEQUENCE LISTING

Figure 1:
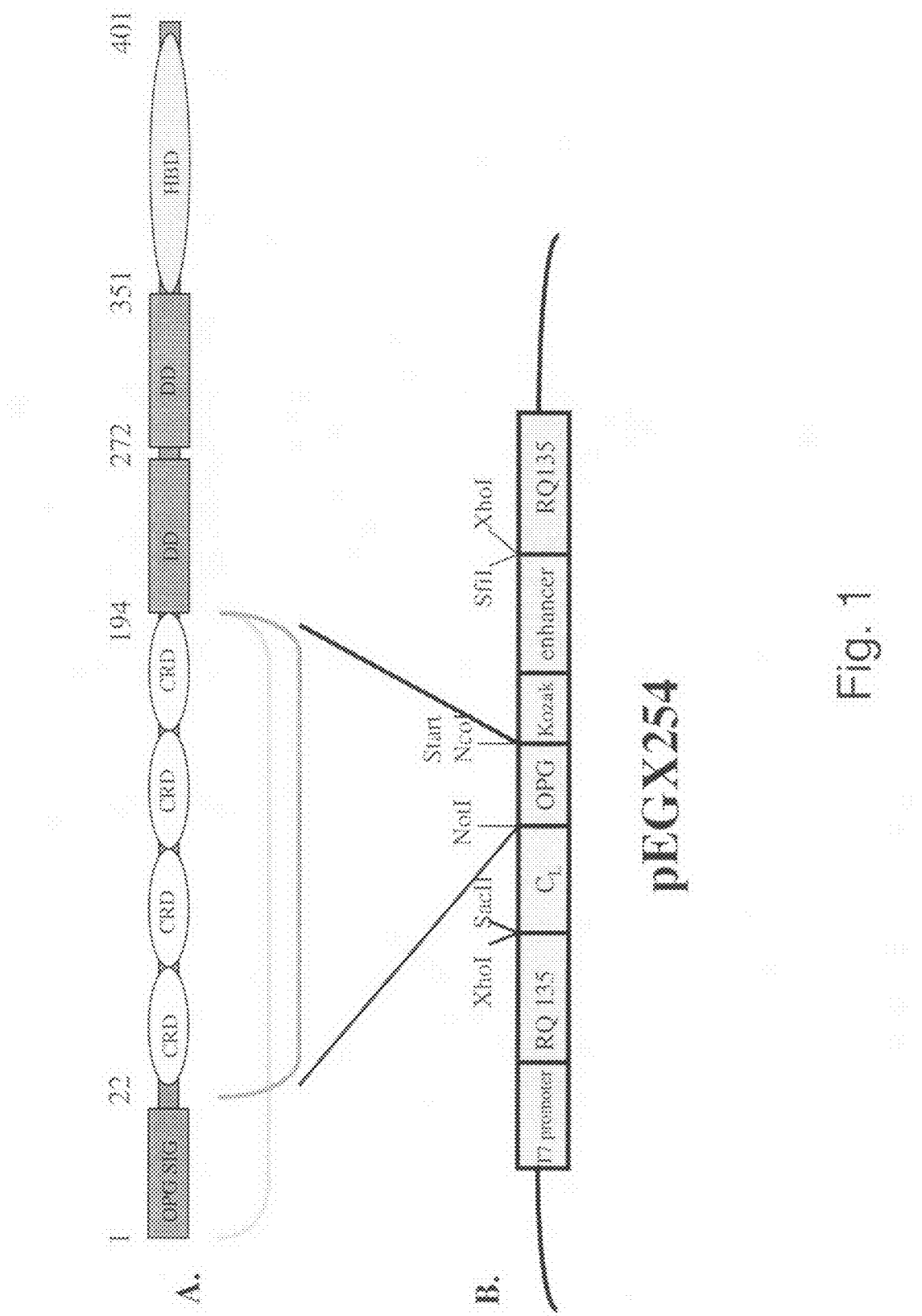
FIG. 1: A. OPG gene structure. CRD-cysteine-rich domain; DD-death domain; HBD: heparin binding domain. B. pEGX254 mutagenesis and display cassette.
Figure 2:
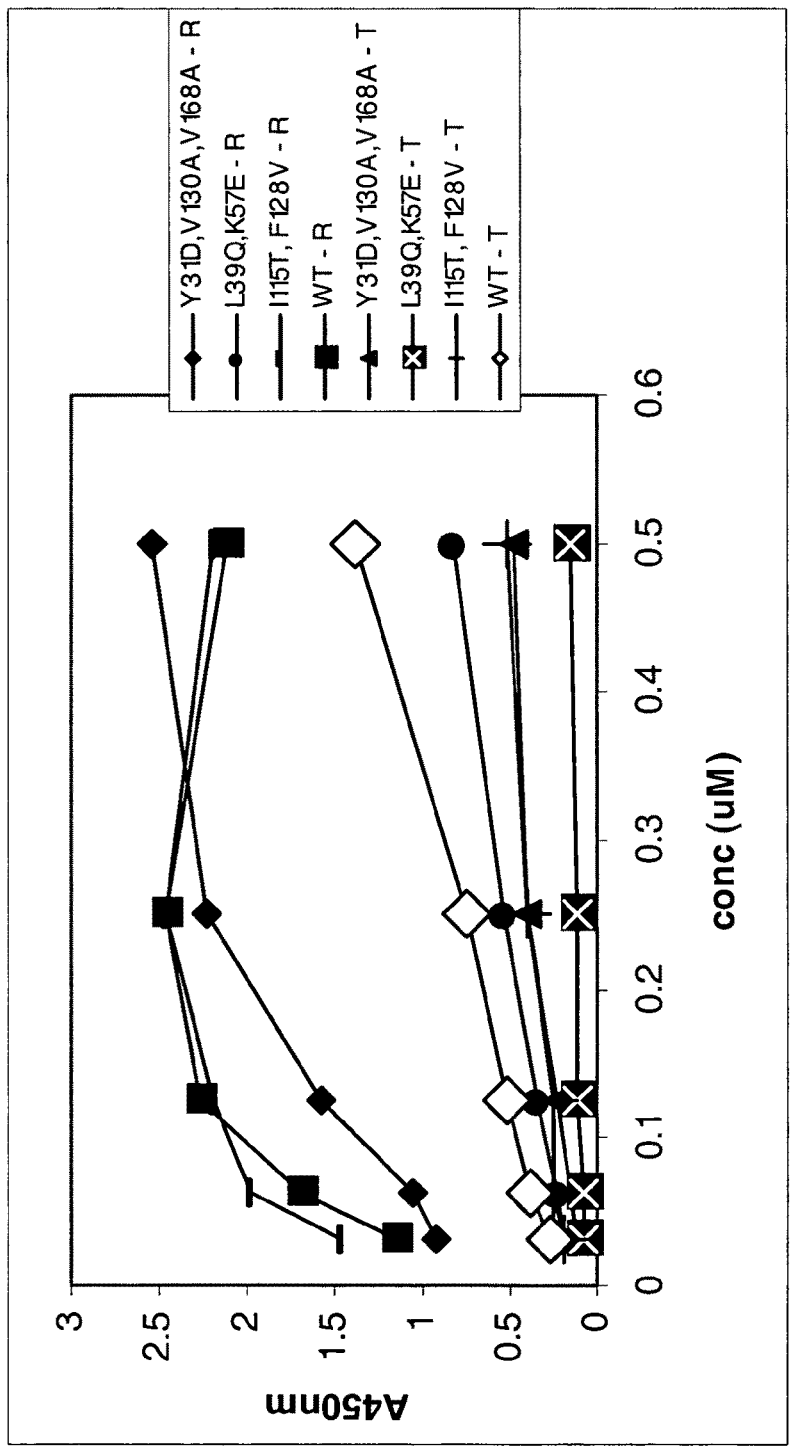
FIG. 2: ELISA comparing binding of purified OVPs and OPG to RANKL and TRAIL. Binding curves are labelled according to the variant number being tested. WT refers to unmutated OPG. Curve labels ending in R refer to RANKL binding; curve labels ending in T refer to TRAIL binding. These studies were carried out using monomeric OPG 22-194 expressed in E. coli.

SEQ ID NO: 1—Human wild-type osteoprotegerin gene;
SEQ ID NO: 2—Human wild-type osteoprotegerin;
SEQ ID NO: 3—Rat wild-type osteoprotegerin;
SEQ ID NO: 4—Mouse wild-type osteoprotegerin; and
SEQ ID NOs: 5 to 47—Human osteoprotegerin variant proteins (OVPs); and
SEQ ID NOs: 48 and 49—Primers used to isolate the OPG gene.

DETAILED DESCRIPTION OF THE PREFERRED EMBODIMENTS

General Techniques

Unless defined otherwise, all technical and scientific terms used herein have the same meaning as commonly understood by one of ordinary skill in the art (e.g., in cell culture, molecular genetics, nucleic acid chemistry, hybridization techniques, chemistry and biochemistry).

Unless otherwise indicated, the recombinant DNA techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. flames (editors), DNA Cloning: A Practical Approach, Volumes 1-4, IRL Press (1995 and 1996), and F. M. Ausubel et al. (Editors), Current Protocols in Molecular Biology, Greene Pub. Associates and Wiley-Interscience (1988, including all updates until present).

Osteoprotegerin (OPG)

OPG is a member of the TNF receptor superfamily, having an activity associated with bone metabolism and in particular having the activity of inhibiting bone resorption thereby increasing bone density. In particular, the interaction of OPG with RANKL inhibits RANKL's ability to stimulate the formation and activity of osteoclasts via its interaction with RANK, and it is this activity of OPG that confers its ability to reduce bone loss.

The biological activities of OPG also include activity associated with binding to TRAIL. TRAIL (TNF-related apoptosis inducing ligand) is a TNF-like cell surface molecule involved in the induction of apoptosis in cancer cells. OPG is seen as one of a small number of decoy receptors for TRAIL, acting to modulate its ability to target cancer cells. OPG is thus expected to have the undesirable effect of enhancing survival of cancer cells if present at a relevant site in sufficient quantities.

Various active fragments of OPG have been described. Yamaguchi et al. (J. Biol. Chem. 273, 5117-5123 (1998)) demonstrated that truncated and deleted variants of OPG retained OPG-like activity, while OPG in both monomer or dimer form retained biological activity (Tomoyasu, A et al., Biochem Biophys Res Commun 245, 382-387 (1998)). Schneeweis et al., (J. Biol. Chem. Oct. 7 2005 (epub)) examined the assembly, state and affinity of OPG for RANKL. They reported that dimerisation of OPG either in full length form where the dimerisation is mediated by non-covalent interactions within the death domain regions, or in truncated form where dimerisation may be mediated by Fc attachment, is required for high affinity attachment of OPG to RANKL.

The amino acid sequences of wild-type human, rat and mouse osteoprotegerin are shown in SEQ ID NOs 2 to 4 respectively.

Wild-type OPG sequences also encompass those that have the amino terminal leader sequence of 21 amino acids removed and/or where amino acids are removed from the C-terminus up to and including amino acid 185.

OPG Variant Proteins

By "protein" herein is meant at least two covalently attached amino acids, which includes proteins, polypeptides, oligopeptides and peptides. The protein may be made up of naturally occurring amino acids and peptide bonds, or synthetic peptidomimetic structures, i.e., "analogs" such as peptoids (see Simon et al., Proc. Natl. Acd. Sci. U.S.A. 89(20: 9367-71 (1992)), generally depending on the method of synthesis. For example, homo-phenylalanine, citrulline, and noreleucine are considered amino acids for the purposes of the invention. "Amino acid" also includes imino acid residues such as proline and hydroxyproline. Both D- and L-amino acids may be utilized.

The present inventors have now generated novel OPG Variant Proteins (OVPs) which demonstrate reduced binding affinity for TRAIL. Importantly, the OVPs of the present invention retain the ability to bind to RANKL. Accordingly, it is envisaged that the OVPs of the present invention will retain the ability of wild-type OPG to modulate bone metabolism, without having the undesired TRAIL-associated characteristic of enhancing survival of cancer cells.

Accordingly, the present invention provides an OPG variant protein comprising at least one modification when compared to wild-type OPG, wherein the OPG variant protein retains binding affinity for RANKL but exhibits reduced binding affinity for TRAIL when compared to wild-type OPG.

By "retains binding affinity for RANKL" we mean that the OPG variant protein exhibits at least 20% binding affinity for RANKL when compared to wild-type OPG.

The wild type OPG may be derived from any species, preferably a mammalian species. In a preferred embodiment, the wild-type OPG is a prevalent human OPG protein. More preferably, the wild type OPG is a protein having an amino acid sequence as is shown in SEQ ID NO:2.

The OPG variant proteins of the present invention preferably exhibit at least one biological activity of wild-type OPG.

In one example, the biological activity of the wild-type OPG relates to bone metabolism, and in particular the ability to inhibit or reduce stimulation and/or activity of osteoclasts by RANKL. Preferably, OPG variant proteins of the present invention retain the ability to prevent disease related decreases in bone density or abnormal bone turnover.

In another example, the biological activity of the wild-type OPG relates to T cell activity, and in particular the ability to reduce or inhibit T cell activation. Preferably, OPG variant proteins of the present invention are useful treatments for autoimmune disorders such as systemic lupus erythematosus, inflammatory bowel disease, diabetes, multiple sclerosis, rheumatoid arthritis, and ankylosing spondylitis.

In further examples, OPG variant proteins of the present invention are useful for treating cardiovascular disease, preventing or reducing calcification of blood vessels and valves, or enhancing blood vessel growth.

In one embodiment the OPG variant protein is a modified version of a full length wild type OPG sequence. In another embodiment, the OPG variant protein contains one or more additional insertions or deletions at the N-terminus, C-terminus, or internally. For example, the OPG variant protein may consist of any modified active fragment of OPG. The active fragment may consist of, for example, amino acids 22-294, amino acids 22-201, 22-194 or amino acids 1-197

In a preferred embodiment, OPG variant proteins have at least 1 amino acid residue that differs from a wild-type OPG sequence, with at least 2, 3, 4, or 5 different residues being more preferred. The modifications are preferably amino acid substitutions and may include those to surface or exposed areas of OPG. OPG variant proteins may comprise one domain or multiple domains connected by linker sequences. OPG variant proteins may contain further modifications, for instance modifications that alter stability or immunogenicity or which enable posttranslational modifications such as PEGylation or glycosylation.

In one preferred embodiment the OPG variant protein comprises at least one modification in the region encompassed by amino acid residues 102-130. For example, the OPG variant protein may comprise at least one amino acid substitution at position 102, 111, 115, 122, 128 or 130.

In one preferred embodiment, the OPG variant protein comprises at least one modification within the loop structure comprising residues 107-118. In a particularly preferred embodiment, the modification in this region involves substitution of Ile at position 115. Ile at position 115 may be substituted by amino acids that are more polar or have shorter side chains. Preferably, Ile at position 115 is substituted with Thr, Met, Val, Asp, Gly, Ser or Arg. Thus, preferred modifications include I115T, I115M, I115V, I115D, I115G, I115S and I115R.

In one preferred embodiment the OPG variant protein comprises at least one modification in the region encompassed by amino acid residues 120-130. In another preferred embodiment, the modification involves substitution of Arg at position 122. Preferably, Arg at position 122 is substituted with Gly, Gln, Ser, Asn or Glu. Thus, preferred modifications include R122G, R122Q, R122S, R122N and R122E.

In yet a further particularly preferred embodiment, the modification involves substitution of Phe at position 128. Preferably, Phe at position 128 is substituted with Val, Ala, Leu, Ile or Ser. Thus, preferred modifications include F128V, F128A, F128L, F128 I and F128S.

In still a further preferred embodiment, the modification involves substitution of Val at position 130. Preferably, Val at position 130 is substituted with Glu or Ala.

In a further preferred embodiment, the OPG variant protein comprises at least two modifications.

The at least two modifications may both occur in the region encompassed by residues 102-130. For example, the at least two modifications may involve substitutions at positions 115 and 122. Examples of suitable double modifications within this region are R122N and I115M; R122N and I115M; F128S and I115M; F128I and I115M; and F128L and I115M.

Alternatively, the at least two modifications may involve one or more modifications within the region encompassed by amino acids 102-130 and one or more modifications outside of this region.

The modification outside of this region may occur at, for example, any one or more of residues 31, 40, 51, 100, 155, 167 or 168. In one preferred embodiment modification occurs at residue 40. Preferably, the modification involves substitution of Leu at position 40 with Ser.

In another embodiment, the OPG variant protein of the present invention comprises one or more modifications within the region encompassed by amino acids 102-130 and a modification to any one or more of the following amino acid residues: Gln21, Glu22, Thr23, Phe24, Pro25, Pro26, Lys27, Tyr28, Leu29, His30, Tyr31, Asp32, Glu33, Glu34, Thr35, Ser36, His37, Gln38, Asp42, Lys43, Pro45, Pro46, Thr48, Lys51, Gln52, His53, Cys54, Thr55, Ala56, Lys57, Trp58, Lys59, Thr60, Val61, Ala63, Pro64, Pro66, Asp67, His68, Tyr69, Asp72, Ser73, Trp74, Thr76, Ser77, Asp78, Glu79, Leu81, Tyr82, Ser84, Pro85, Val86, Lys88, Glu89, Leu90, Tyr92, Val93, Lys94, Gln95, Glu96, Asn98, Arg99, Thr100, His101, Val131, Gln132, Ala133, Gly134, Thr135, Pro136, Glu137, Arg138, Val141, Lys143, Arg144, Cys145, Pro146, Asp147, Gly148, Phe149, Phe150, Ser151, Asn152, Glu153, Thr154, Ser155, Ser156, Lys157, Ala158, Pro159, Cys160, Arg161, Lys162, His163, Thr164, Asn165, Cys166, Ser167, Val168, Phe169, Gly170, Leu171, Leu172, Leu173, Thr174, Gln175, Lys176, Gly177, Asn178, Ala179, Thr180, His181, Asp182, Asn183, Ile184, Cys185, Ser186, Gly187, Asn188, Ser189, Glu190, Ser191, Thr192, Gln193, Lys194, Cys195, Gly196, Ile197, Asp198, Val199, Thr200 and Leu201.

In another embodiment, the OPG variant protein of the present invention comprises one or more modifications within the region encompassed by amino acids 102-130 and a modification to any one or more of the following amino acid residues: Tyr28, His30, Tyr31, Glu34, Thr35, Ser36, His 37, Lys43, Tyr49, Gln52, His53, Pro66, Asp67, His68, Tyr69, Tyr70, Thr71, Asp72, Ser73, Trp74, His75, Thr76, Ser77, Asp78, Glu79, Cys80, Leu81, Tyr82, Cys83, Ser84, Pro85, Val86, Cys87, Lys88, Glu89, Leu90, Gln91, Asn139 and Glu153.

The present invention also provides an OPG variant protein comprising a modification at residue 40, wherein the OPG variant protein retains binding affinity for RANKL but exhibits reduced binding affinity for TRAIL when compared to wild-type OPG. Preferably, the modification involves substitution of Leu at position 40 with Ser.

An OPG variant protein of the present invention may involve any one or more of the modifications shown in Table 1.

In a further preferred embodiment the OPG variant protein comprises a sequence as shown in any one of SEQ ID Nos: 5 to 47.

In a further preferred embodiment of the present invention, the OVP exhibits a binding affinity for RANKL that is at least 50%, more preferably at least 60%, more preferably at least 70%, more preferably at least 80%, more preferably at least 90% and more preferably at least 95% that of wild type OPG.

In one embodiment, the OVP exhibits increased binding affinity for RANKL when compared to wild-type OPG.

In a further preferred embodiment, the OVP has an EC50 (nM) for attachment to RANKL of less than 5 nM, more preferably less than 1 nM under assay conditions as described in Example 8.

In a further preferred embodiment of the present invention, the OVP exhibits a binding affinity for TRAIL that is less than 50%, more preferably less than 40%, more preferably less than 30%, more preferably less than 20%, more preferably less than 10% and more preferably less than 5% that of wild type OPG.

In a further preferred embodiment, the OVP has an EC50 (nM) for attachment to TRAIL of greater than 5 nM, more preferably greater than 10 nM, more preferably greater than 25 nM, more preferably greater than 50 nM under assay conditions as described in Example 8.

Also encompassed are OPG variant proteins having deletions or carboxy-terminal truncations of part or all of amino acids residues 195-401 or 198-401 of OPG; one or more amino acid changes in residues 195-401 or 198-401; deletion of part or all of a cysteine-rich domain of OPG, in particular deletion of the distal (carboxy-terminal) cysteine-rich domain; and one or more amino acid changes in a cysteine-rich domain, in particular in the distal (carboxy-terminal) cysteine-rich domain.

Preferred amino acid sequence deletions generally range from about 1 to 30 residues, more preferably about 1 to 10 residues and typically about 1 to 5 contiguous residues.

It will be understood that the amino acid numbering used herein to refer to sites for mutagenesis relates to numbering of the human OPG sequence shown in SEQ ID NOs: 1 and 2. Corresponding sites in homologues, derivatives and allelic variants are also encompassed by the present invention.

The term "corresponding to" is used in the context of the present invention to refer to amino acid residues of OPG polypeptides related to SEQ ID NOs 1 and 2 (for example greater than 70% identical, greater than 80% identical, greater than 90% identical or greater than 95% identical to SEQ ID NOs 1 and 2), however, the relative residue numbering of the related polypeptide may be different to that of SEQ ID NOs 1 and 2.

Also encompassed are OPG variant proteins described herein comprising additional conservative substitutions throughout the sequence. Such conservative substitutions are as follows:

| Original Residue | Exemplary Substitutions |
| --- | --- |
| Ala (A) | val; leu; ile; gly |
| Arg (R) | lys |
| Asn (N) | gln; his; |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe; |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

Furthermore, if desired, non-naturally occurring amino acids or chemical amino acid analogues can be introduced as a substitution or addition into the polypeptide of the present invention. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

Also provided by the invention are chemically modified derivatives of OPG variant proteins which may provide additional advantages such as increasing stability and circulating time of the polypeptide, or decreasing immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. Also included are OVPs of the present invention which are differentially modified during or after synthesis, e.g., by biotinylation, benzylation, glycosylation, acetylation, phosphorylation, amidation, derivatization by known protecting/blocking groups, proteolytic cleavage, etc. The polypeptides may be modified at random positions within the molecule, or at predetermined positions within the molecule and may include one, two, three or more attached chemical moieties. These modifications may serve to increase the stability and/or bioactivity of the polypeptide of the invention.

Additional modifications of OPG variant proteins encompassed by the invention include post-translational modifications (e.g., N-linked or O-linked carbohydrate chains, processing of N-terminal or C-terminal ends), chemical modifications of N-linked or O-linked carbohydrate chains, and addition of an N-terminal methionine residue as a result of procaryotic host cell expression. The OVPs may also be modified with a detectable label, such as an enzymatic, fluorescent, isotopic or affinity label to allow for detection and isolation of the protein.

Further modifications of OPG variant proteins include chimeric proteins wherein the OPG variant protein is fused to a heterologous amino acid sequence. The heterologous sequence may be any sequence which allows the resulting fusion protein to retain at least the activity of the OPG variant protein. The heterologous sequences include for example, immunoglobulin fusions, such as Fc fusions, or fusions to other cellular ligands which may increase stability or aid in purification of the protein.

In one embodiment, OPG variant proteins of the invention may be produced as dimeric or even as oligomeric single-chain molecules, with two, three or possibly more monomers.

The monomers may be joined by a peptide bond or a peptide linker, or for example, by means of a PEG molecule.

Dimerisation can also be achieved by producing the compound as a fusion protein with the Fc-portion of Ig gamma 1 (GenPept accession No. M87789.1). The molecules can be expressed as fusion proteins with a C-terminal Fc-part or with a N-terminal Fcpart.

Dimerisation can also be achieved by fusing the product candidate to a GCN4 leucine zipper, which has been reported to induce dimerisation of fusion proteins (Donate, et al., Biochemistry, 39 11467-76 (2000)).

Alternatively, dimeric molecules may be produced by mutagenizing one of the last five, or alternatively one of the first five amino acid residues to a cysteine residue. An unpaired cysteine residue of the purified compound can then be attached to a "di-active" PEG group by using existing thiol reactive attachment groups. Alternatively, dimeric molecules can be produced by inserting two candidate molecules (identical or even different) in-frame with a suitable flexible polypeptide linker in an appropriate expression vector.

Still further modifications of OPG variant proteins include dimeric or multimeric forms where the monomeric units of the OPG variant protein may be linked together chemically or genetically by appropriate linker molecules which may include peptide or chemical linkers, or disulphide bridges between cysteine residues. Additionally, dimeric or multimeric forms of the subject proteins may be achieved by linkages between proteins to which the OPG protein is fused, such as Fc regions.

The OPG variant proteins of the invention are preferably isolated and purified from other polypeptides present in tissues, cell lines and transformed host cells expressing the OVP, or purified from components in cell cultures containing the secreted protein. In one embodiment, the OVP is free from association with other proteins, such as the expression product of a bacterial host cell.

OPG variant proteins of the present invention can be prepared using any technique known in the art. For example, the polynucleotide provided as SEQ ID NO: 1 can be subjected to in vitro mutagenesis. Such in vitro mutagenesis techniques include sub-cloning the polynucleotide into a suitable vector, transforming the vector into a "mutator" strain such as the *E. coli* XL-1 red (Stratagene) and propagating the transformed bacteria for a suitable number of generations. In another example, the polynucleotides of the invention are subjected to DNA shuffling techniques as broadly described by Harayama (1998). Protein products derived from mutated/altered DNA can readily be screened using techniques described herein to determine if they have enhanced and/or altered substrate specificity.

Amino acid sequence mutants of the polypeptides of the present invention can also be prepared by introducing appropriate nucleotide changes into a nucleic acid sequence, or by in vitro synthesis of the desired polypeptide. Such mutants include, for example, deletions, insertions or substitutions of residues within the amino acid sequence. A combination of deletion, insertion and substitution can be made to arrive at the final construct, provided that the final protein product possesses the desired characteristics.

Substitution mutants have at least one amino acid residue in the wild-type OPG sequence removed and a different residue inserted in its place. The sites of greatest interest for substitutional mutagenesis include those sites exemplified herein. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Alternatively, OPG variant proteins can be generated using a cell-free in vitro evolution mutagenesis system. In one example of cell-free in vitro evolution, a system similar to that described in WO 99/58661 or WO 2004/039995 is utilized.

A cell-free in vitro evolution method comprises exposing mutant OPG RNA molecules, produced directly or indirectly by the action of a polymerase in the presence of a mutagen (such QB replicase or ribavirin, or a derivative/analogue thereof) to a translation system under conditions which result in the production of a population of mutant proteins. These mutant OPG proteins are linked to the RNA from which they were translated forming a population of mutant protein/RNA complexes. This population of mutant OPG protein/RNA complexes is screened for a desired biological activity such as binding to RANKL without binding to TRAIL. A mutant protein/RNA complex with the desired activity can be isolated and the sequence of the protein encoded by the RNA characterized by standard techniques.

The present invention also provides a process for preparing an OPG variant protein of the invention, the process comprising cultivating a host cell of the invention under conditions which allow production of the OPG variant protein, and recovering the OPG variant protein. Such cells can be used for the production of commercially useful quantities of the encoded OPG variant protein.

OPG variant proteins of the present invention can be produced in a variety of ways, including production and recovery of natural proteins, production and recovery of recombinant proteins, and chemical synthesis of the proteins. In one embodiment, an OPG variant protein of the present invention is produced by culturing a cell capable of expressing the OPG variant protein under conditions effective to produce the OPG variant protein, and recovering the OPG variant protein. Effective culture conditions include, but are not limited to, effective media, bioreactor, temperature, pH and oxygen conditions that permit protein production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

A method for the purification of OPG variant proteins from transfected host cells is also included. The purification process may employ one or more standard protein purification steps, such as chromatography, in an appropriate order to obtain purified protein. The chromatography steps can include ion exchange, gel filtration, hydrophobic interaction, reverse phase, chromatofocusing, affinity chromatography employing an anti-OPG antibody or biotin-streptavidin affinity complex and the like.

The present invention also provides a method for reducing the binding affinity of OPG for TRAIL, the method comprising modifying at least one amino acid within an OPG protein or fragment thereof to produce an OPG variant protein, and testing the OPG variant protein for binding affinity for TRAIL.

In one preferred embodiment the method comprises modifying at least one amino acid within the region encompassed by residues 102-130 of wild type OPG to produce an OPG variant protein, and testing the OPG variant protein for binding affinity for TRAIL.

Methods for testing the OPG variant protein for binding affinity for TRAIL will be known to those skilled in the art. Suitable assays include, but are not limited to, quantitative comparisons comparing kinetic and equilibrium binding constants. The kinetic association rate (Kon) and dissociation rate (Koff), and the equilibrium binding constants (Kd) may be determined using surface plasmon resonance on a BIAcore instrument following the standard procedure in the literature (Pearce et al., Biochemistry 38:81-89 (1999)). Several alternative methods can also be used to determine binding affinity and kinetics, examples of which are described in the Example section herein.

Nucleic Acids, Vectors and Host Cells

The present invention also provides an isolated polynucleotide encoding an OPG variant protein of the present invention. Examples of polynucleotides of the invention include cDNA, genomic DNA, synthetic DNA and RNA.

Preferably, the polynucleotide is a variant of SEQ ID NO: 1, wherein the variant comprises nucleic acid changes such that it encodes the desired OPG variant protein of the invention. Methods of producing such nucleic acid changes are known in the art and are also described herein.

The present invention also provides a vector which comprises a polynucleotide according to the invention. Preferably, the vector is suitable for the replication and/or expression of a polynucleotide. The vectors may be, for example, a plasmid, virus or phage vector provided with an origin of replication, and preferably a promoter for the expression of the polynucleotide and optionally a regulator of the promoter. The vector may contain one or more selectable markers, for example an ampicillin resistance gene in the case of a bacterial plasmid or a neomycin resistance gene for a mammalian expression vector. The vector may be used in vitro, for example for the production of RNA or used to transfect or transform a host cell.

The present invention also provides a host cell which comprises a vector according to the invention, or contains the gene encoding one of the proteins of the invention under conditions that allow expression and production of the subject protein.

The nucleic acids of the invention may be constructed using evolutionary or site-directed mutagenesis techniques available to the skilled worker. The starting material may be, for example, cDNA or genomic DNA encoding wild-type OPG. cDNA is obtained from libraries prepared from mRNA isolated from various tissues expressing Osteoprotegerin. In humans, tissue sources for Osteoprotegerin include kidney, liver, placenta and heart. Genomic DNA encoding Osteoprotegerin is obtained from genomic libraries which are commercially available from a variety of species.

Alternatively, the nucleic acids of the invention may be synthetic nucleic acids. Synthetic DNA, for example, is obtained by chemical synthesis of overlapping oligonucleotide fragments followed by assembly of the fragments to reconstitute part or all of the coding region and flanking sequences (see U.S. Pat. No. 4,695,623 describing the chemical synthesis of interferon genes). RNA is obtained most easily by procaryotic expression vectors or by in vitro constructs which direct high-level synthesis of mRNA, such as vectors using T7 promoters and RNA polymerase.

Expression vectors containing nucleic acid sequences encoding OVPs, host cells transformed with said vectors and methods for the production of OVPs are also provided by the invention. An overview of expression of recombinant proteins is found in Methods of Enzymology Vol. 185 (Goeddel, D. V. ed.) Academic Press (1990).

Host cells for the production of OVPs include procaryotic host cells, such as E. coli, yeast, plant, fungal, insect and mammalian host cells. E. coli strains such as HB101 or JM101 are suitable for expression. Preferred mammalian host cells include COS, CHOd-, 293, CV-1, 3T3, baby hamster kidney (BHK) cells and others. Mammalian host cells are preferred when post-translational modifications, such as glycosylation and polypeptide processing, are important for OVP activity. Mammalian expression allows for the production of secreted polypeptides which may be recovered from the growth medium.

Vectors for the expression of OVPs preferably contain at a minimum sequences required for vector propagation and for expression of the cloned insert. These sequences include a replication origin, selection marker, promoter, ribosome binding site, enhancer sequences, RNA splice sites and transcription termination site. Vectors suitable for expression in the aforementioned host cells are readily available and the nucleic acids of the invention are inserted into the vectors using standard recombinant DNA techniques. Vectors for tissue-specific expression of Osteoprotegerin are also included. Such vectors include promoters which function specifically in liver, kidney or other organs for production in mice, and viral vectors for the expression of Osteoprotegerin in targeted human cells.

Using an appropriate host-vector system, an OVP may be produced recombinantly by culturing a host cell transformed with an expression vector containing nucleic acid sequences encoding the OVP under conditions such that the OVP is produced, and isolating the product of expression. The OVP may be produced in the supernatant of transfected mammalian cells or in inclusion bodies of transformed bacterial host cells. OVP so produced may be purified by procedures known to one skilled in the art as described below. The expression of OVP in E. coli is described in Example 2. The specific plasmids and host cells described in this Example are for illustrative purpose only, however, and it will be appreciated that other available plasmids and host cells could also be used to express OVPs of the invention.

Pharmaceutical Compositions

The present invention provides a composition for inhibiting or reducing binding of RANK to RANKL, the composition comprising an OPG variant protein according to the invention, and one or more acceptable carriers.

The present invention also provides a composition for inhibiting or reducing a biological effect mediated through the interaction of RANK and RANKL, the composition comprising an OPG variant protein according to the invention, and one or more acceptable carriers.

The present invention also provides a composition for inhibiting or reducing stimulation of osteoclasts by RANKL, the composition comprising an OPG variant protein according to the invention, and one or more acceptable carriers.

The present invention also provides a pharmaceutical composition comprising a therapeutically effective amount of an OPG variant protein according to the invention and one or more of a pharmaceutically acceptable carrier, solubilizer, stabilizer and anti-oxidant.

The term "therapeutically effective amount" means an amount which provides a therapeutic effect for a specified condition and route of administration. The composition may be in a liquid or lyophilized form and comprises a diluent (Tris, acetate or phosphate buffers) having various pH values and ionic strengths, solubilizer such as Tween or Polysorbate, carriers such as human serum albumin or gelatin, preservatives such as thimerosal or benzyl alcohol, and antioxidants such as ascorbic acid or sodium metabisulfite. Also encompassed is a composition comprising an OVP modified with water soluble polymers to increase solubility or stability. Compositions may also comprise incorporation of OPVs into liposomes, microemulsions, micelles or vesicles for controlled delivery over an extended period of time. Selection of a particular composition will depend upon a number of factors, including the condition being treated, the route of administration and the pharmacokinetic parameters desired. A more extensive survey of component suitable for pharmaceutical compositions is found in Remington's Pharmaceutical Sciences, 18th ed. A. R. Gennaro, ed. Mack, Easton, Pa. (1980).

Compositions of the invention may be administered by injection, either subcutaneous, intravenous or intramuscular, or by oral, nasal, pulmonary or rectal administration. The route of administration eventually chosen will depend upon a number of factors and may be ascertained by one skilled in the art.

The invention also provides for pharmaceutical compositions comprising a therapeutically effective amount of the nucleic acids of the invention together with a pharmaceutically acceptable adjuvant. Nucleic acid compositions will be suitable for the delivery of part or all of the OVP to cells and tissues as part of a gene therapy regimen.

By "gene therapy" herein is meant the one time or repeated administration of a therapeutically effective DNA, mRNA, or other nucleic acid. In one embodiment, genes are introduced into cells in order to achieve in vivo synthesis of a therapeutically effective genetic product.

Methods of Treatment

OPG has undergone preclinical and clinical testing with potential for application in various conditions associated with increased bone turnover and bone loss, including osteoporosis, rheumatoid arthritis, Paget's disease, periodontal disease, vascular disease and cancers that are located in or have metastasised to bone (For review, see Lorenz et al., J. Amer Med Assoc 292: 490-5 (2004) and references therein).

It is also known that antagonizing RANK signaling could be a treatment for autoimmune disorders such as systemic lupus erythematosus, inflammatory bowel disease, diabetes, multiple sclerosis, rheumatoid arthritis, and ankylosing spondylitis.

Recent reports also indicate that OPG may also be used in the treatment or prevention of cardiovascular disease, to prevent or reduce calcification of blood vessels and valves (Kaden et al., J. Mol. Cardiol. 36: 17-19 (2004) and for encouraging blood vessel growth (Cross et al; Int J Cancer Nov. 14, 2005 (epub)). Polymorphisms in the OPG gene have been associated with the occurrence of Juvenile Pagets disease (Daroszewska et al., J. Bone Miner. Res 19: 1506-11 (2004)) and with Caucasian men at high risk of developing coronary artery disease (Soufi et al., J. Clin. Endocrinol. Metab. 89: 3764-8 (2004)).

It is clear, therefore, that the OPG variant proteins of the present invention will have a range of therapeutic uses.

Accordingly, the present invention provides a method for inhibiting or reducing binding of RANK to RANKL, the method comprising exposing a RANKL molecule to an OPG variant protein according to the present invention.

The present invention also provides a method for inhibiting or reducing a biological effect mediated through the interaction of RANK and RANKL in a cell, the method comprising exposing the cell to an OPG variant protein according to the present invention.

The present invention also provides a method for inhibiting or reducing a biological effect mediated through the interaction of RANK and RANKL in a subject, the method comprising administering to a subject an OPG variant protein according to the invention.

The present invention also provides a method for treatment or prevention of an autoimmune or immune-mediated inflammatory disease in a subject, the method comprising administering to a subject an OPG variant protein according to the invention.

The present invention also provides a method for treatment or prevention of cardiovascular disease in a subject, the method comprising administering to a subject an OPG variant protein according to the invention.

The present invention also provides a method for inhibiting or reducing differentiation, activation and/or survival of osteoclasts by RANKL, the method comprising exposing tissue containing osteoclasts or osteoclast precursors to an OPG variant protein according to the invention.

The present invention also provides a method for inhibiting or reducing differentiation, activation and/or survival of osteoclasts by RANKL in a subject, the method comprising administering to a subject an OPG variant protein according to the invention.

By "subject" herein is meant both humans and other animals, particularly mammals as outlined herein, with humans being preferred.

The present invention also provides method for preventing or treating a bone disorder comprising administering to a patient the pharmaceutical composition of the present invention.

The terms "treating" and "treatment" herein are meant to include therapeutic treatment, as well as prophylactic, or suppressive measures for the disease or disorder. Thus, for example, successful administration of an OPG variant protein prior to onset of the disease may result in treatment of the disease. As another example, successful administration of an OPG variant protein after clinical manifestation of the disease to combat the symptoms of the disease comprises "treatment" of the disease. "Treatment" also encompasses administration of an OPG variant protein after the appearance of the disease in order to eradicate the disease. Successful administration of an agent after onset and after clinical symptoms have developed, with possible abatement of clinical symptoms and perhaps amelioration of the disease, further comprises "treatment" of the disease.

Conditions which are treatable with OVPs of the present invention include the following:

Osteoporosis, such as primary osteoporosis, endocrine osteoporosis (hyperthyroidism, hyperparathyroidism, Cushing's syndrome, and acromegaly), hereditary and congenital forms of osteoporosis (osteogenesis imperfecta, homocystinuria, Menkes' syndrome, and Riley-Day syndrome) and osteoporosis due to immobilization of extremities.

Paget's disease of bone (osteitis deformans) in adults and juveniles.

Osteomyelitis, or an infectious lesion in bone, leading to bone loss.

Hypercalcemia resulting from solid tumors (breast, lung and kidney) and hematologic malignancies (multiple myeloma, lymphoma and leukemia); idiopathic hypercalcemia, and hypercalcemia associated with hyperthyroidism and renal function disorders.

Osteopenia following surgery, induced by steroid administration, and associated with disorders of the small and large intestine and with chronic hepatic and renal diseases.

Osteonecrosis, or bone cell death, associated with traumatic injury or non-traumatic necrosis associated with Gaucher's disease, sickle cell anaemia, systemic lupus erythematosus and other conditions.

Bone loss due to rheumatoid arthritis, ankylosing spondylitis and other immune-mediated inflammatory disorders.

Calcification of the vascular system.

Periodontal bone loss.

Cancers that affect bone including multiple myeloma, primary cancer of the bone and osteolytic metastasis such as from metastasised breast and prostate cancer.

Cardiovascular disease.

Coronary artery disease.

Autoimmune disorders such as systemic lupus erythematosus, inflammatory bowel disease, diabetes, multiple sclerosis, rheumatoid arthritis, and ankylosing spondylitis.

It will be appreciated that an OVP of the invention may be used alone or in conjunction with other therapeutic agents. For example, an OVP of the present invention may be used in conjunction with a therapeutically effective amount of a TRAIL activator antibody or an anti-TNF antibody.

In one preferred embodiment the OPG variant protein of the present invention is used to treat a bone disorder that is associated with excessive bone turnover or loss. The bone disorder may include, but is not limited to, osteoporosis, Paget's disease of the bone, hypercalcemia, hyperpararthyroidism, steroid-induced osteopenia, rheumatoid arthritis, osteomyelitis, multiple myeloma, bone cancer, vascular calcification, osteolytic metastasis, and periodontal bone loss.

It is understood that the OVP of the invention may be used alone or in conjunction with other factors for the treatment of bone disorders.

In one embodiment, the OVP is used in conjunction with a therapeutically effective amount of a factor which stimulates bone formation. Such factors include but are not limited to the bone morphogenic factors designated BMP-1 through BMP-12, transforming growth factor-β. (TGF-β) and TGF-β family members, interleukin-1 inhibitors, TNFα inhibitors, parathyroid hormone and analogs thereof, parathyroid related protein and analogs thereof, Vitamin E series prostaglandins, bisphosphonates (such as alendronate and others), and bone-enhancing minerals such as fluoride and calcium.

The invention will now be described in more detail by reference to the following non-limiting Examples.

EXAMPLE 1

Cloning the Human OPG Gene

The gene for OPG was isolated from a human fetal kidney cDNA library (Spring Bioscience, Fremont, Calif.). Primers to the 5' and 3' ends of the OPG sequence were designed and standard PCR used to amplify the gene. The primers used to isolate the OPG gene were:

```
Forward:
                                         (SEQ ID NO: 48)
5'TATTACTCGCGGCCCAGCCGGCCATGAACAAGTTGCTGTGCTGCGCGC

TCG 3'

Reverse:
                                         (SEQ ID NO: 49)
5'CATCTTTATAATCTGCGGCCGCTAAGCAGCTTATTTTTACTGATTGGA

CC 3'.
```

Overhangs in the primers incorporated restriction sites allowing cloning into suitable vectors for propagation in *E. coli* such as pGC (Coia et al., (1996), *J. Immunol. Meth.* 192:13-23) with successful cloning confirmed by DNA sequencing. In addition to the 1203 nucleotides encoding the full-length 401 as OPG protein, the OPG sequence excluding its signal peptide (aa 1-21) was amplified (OPG 22-401). The N-terminal half of the protein to aa 194, comprising the 4 Cys-rich domains, with and without its signal peptide, was also amplified. A schematic representation of the OPG gene structure is shown in FIG. 1A.

The fragment OPG 22-194, which encompasses the part of the protein responsible for binding to RANKL and TRAIL (Simonet et al., (1997), Yamaguchi et al., (1998) as referenced above) was expressed in 2 L of 2×YT/100 μg/mL ampicillin with IPTG induction out of the pGC vector. This produces the protein with a C-terminal double FLAG peptide tag fusion for detection and affinity purification from *E. coli* periplasmic extracts. Induction was carried out for 3-4 h at 20-22° C. Affinity purified material was further peak purified by gel filtration chromatography on a Superdex 200 column. Peaks corresponding in size to an OPG monomer were collected. A smaller peak, corresponding in size to an OPG dimer was also purified. The purified peaks could be detected by Western blot using an anti-FLAG antibody migrating at approximately the expected size. The purified monomeric protein was detected by specific antibodies supplied with an OPG detection kit (R&D systems, Minneapolis, Minn.). The identity of this protein was confirmed by N-terminal amino acid sequencing of its first 19 residues that correlate with the published sequence.

EXAMPLE 2

Generation of OPG Variant Proteins (OVPs)

To create a library of OPG variants, the OPG(22-194) DNA sequence was cloned into the pEGX mutagenesis and display vector (FIG. 1B) with confirmation by DNA sequencing. The OPG-containing plasmid (~0.5-1.0 μg) was linearised by SmaI digestion and 100-200 ng of this was used directly as template for T7 RNA polymerase transcription at 37° C. for 16-24 h. The success of the transcription was verified by agarose gel electrophoresis loading 1 μL, of the 20 μL reaction. Where possible, all manipulations involving RNA, including ribosome display, use DEPC-treated buffers, reagents, and tubes to minimise RNA degradation.

The RNA transcript is used directly as template for a replication reaction by Qβreplicase at 37° C. for 16-24 h:

|  | volume (μL) |
|---|---|
| T7 RNA transcript | 0.5 |
| 25 mM rNTPs | 1 |
| 5 X T7 polymerase buffer | 4 |
| 100 mM DTT | 2 |
| 100 mM MgSO$_4$ | 0-1.6 |
| Qβreplicase | 1 |
| H$_2$0 | 10.5-8.9 |

The success of the replication was assessed by agarose gel electrophoresis loading 1 μL of the reaction. This process generates a double stranded RNA library encoding variants of OPG. Mutation conditions were adjusted to obtain 1-3 random mutations per gene copy. At this stage 1 μg of the OPG RNA library being prepared for display is equivalent to approximately 7×10$^{11}$ molecules. The concentration of the sample is then estimated spectrophotometrically.

The OPG RNA library was then used for ribosome display. The library was first translated for 30 min at 30° C. using a rabbit reticulocyte lysate translation system (Promega):

|  | volume (μL) |
|---|---|
| Reticulocyte lysate | 33 |
| Amino acid mix minus Leu | 0.5 |
| Amino acid mix minus Met | 0.5 |
| 25 mM MgCl$_2$ | 0.5 |
| RNasin | 0.5 |
| KCl | 1.5 |
| OPG RNA | 1-2 μg |
| H$_2$O | to 50 μL |

The absence of a stop codon at the end of the C$_L$ spacer domain stalls the ribosome at the end of translation leading to an RNA/ribosome/protein complex. On completion of translation these complexes were stabilised by keeping cold (on ice) and with the addition of magnesium acetate (MgOAc). The translation was diluted to 300 μL with addition of 60 μL ice-cold PBS/50 mM MgOAc/10% skim milk (biotin-free) and 190 μL PBS/50 mM MgOAc/0.05% Tween/2.5 mg/mL heparin. This mix was then split into 3×100 μL aliquots.

EXAMPLE 3

Panning OVPs

The complexes generated in Example 2 were panned against RANKL (Roche) and TRAIL (Peprotech) in solution. Biotinylated versions of RANKL and TRAIL were prepared using Sulfo-NHS-LC-biotin (Pierce) to enable capture of selected complexes in solution using streptavidin coated magnetic beads (Dynal).

Figure 3:
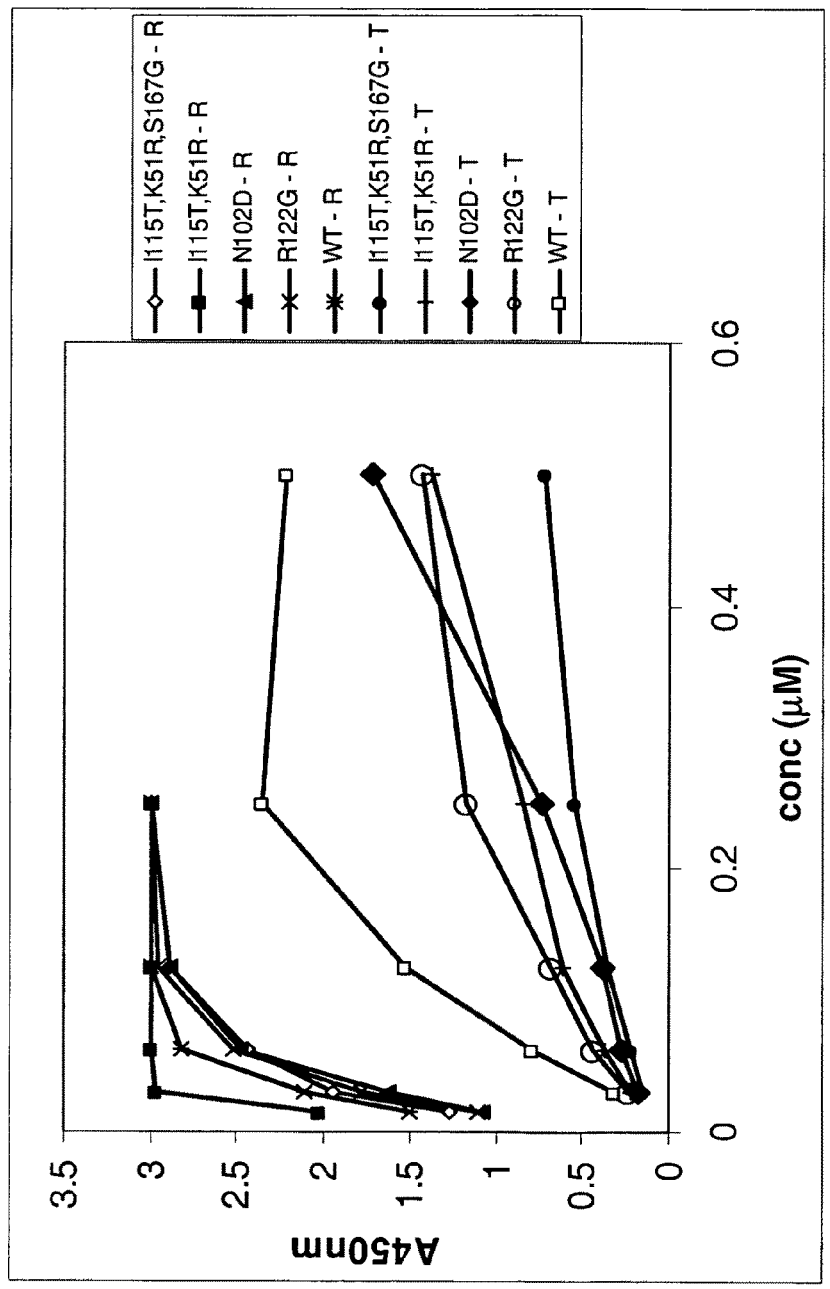
FIG. 3: ELISA comparing binding of purified OVPs and OPG to RANKL and TRAIL. Curve labelling and conditions as for FIG. 3.

A panning reaction was carried out in each of the three translation mix aliquots. Two different strategies were employed to create a selection pressure favouring the isolation of OVP sequences that have amino acid changes in residues that reduce binding affinity to TRAIL, whilst retaining RANKL-binding affinity. One strategy used was to first pan against soluble RANKL, and then TRAIL binders were competed off with an excess of free TRAIL protein. In one translation aliquot, biotinyl-RANKL was added at a concentration that is approximately equimolar to the amount of input RNA. This mix was then rotated for 40-60 min at 4° C. Streptavidin coated magnetic beads (Dynal) were washed and resuspended in PBS/50 mM MgOAc/0.05% Tween. After the RANKL pan, 10 μL of these beads were added to the mix for 10 min at 4° C. The beads that captured biotinyl-RANKL in complex with ribosome-displayed OPG were then washed using a magnet, twice with PBS/50 mM MgOAc/0.05% Tween, twice with PBS/50 mM MgOAc, then resuspended in 100 μL of this buffer. An excess of soluble TRAIL was added to this mix at 2 or more times the molar concentration of the added RANKL to compete off TRAIL binders and this was rotated at 4° C. for 30 min. Any complexes eluted from the beads during this procedure were then washed away as above and the beads with bound RANKL-binding complexes resuspended in 20 μL of $H_2O$. This panning strategy was denoted "RANKL-$1^{st}$".

The other strategy used was to first pan against soluble TRAIL to remove the stronger TRAIL binders, and then pan the mix against RANKL to isolate the RANKL binders remaining. To a second translation aliquot, biotinyl-TRAIL was added at approximately ½ to ¼ of the molar amount of input RNA. This mix was rotated for 40-60 min at 4° C., then 10 μL of streptavidin beads added for 10 min. The beads that captured biotinyl-TRAIL in complex with ribosome-displayed OVPs were removed using a magnet, thereby ridding the mix of the better TRAIL binders. Biotinyl-RANKL was then added to the mix at approximately ½ the molar amount of input RNA and this was rotated at 4° C. for 30-40 min for selection of OPG variants that retain RANKL-binding affinity. The beads were then washed as above and resuspended in $H_2O$. This panning strategy was denoted "TRAIL-$1^{st}$". A control pan was carried out in a third translation aliquot as performed for the RANKL-$1^{st}$ pan but biotinyl-IGF-I (Gropep) was used in place of biotinyl-RANKL. A variation of the RANKL-$1^{st}$ and TRAIL-$1^{st}$ selection strategies described above was also performed where the antigens used were coupled to epoxy magnetic beads (Dynal) instead of using the antigens in soluble biotinylated form.

EXAMPLE 4

Cloning of selected OVPs

RNA selected with the complexes was converted to cDNA using RT-PCR by standard methods using 5 μL of the bead suspension as template. The RT-PCR products were isolated by agarose electrophoresis. As well as bands for the TRAIL-$1^{st}$ and RANKL-$1^{st}$ pans, a weak band can be seen generated from the IGF-I pan, suggesting that there is some non-specific selection inherent within this selection procedure. The pool of selected DNAs were then purified from the gel and restriction digested and ligated into the expression vector pGC so that screening for the desired binding properties could proceed. The ligations were electroporated into an appropriate *E. coli* strain to produce transformant colonies.

EXAMPLE 5

Screening OVP Clones

About 100 clones from each display and selection experiment were screened. Clones carrying the genes for OVPs are grown as starter cultures in 200 μL of 2×YT supplemented with ampicillin and glucose in wells of microtitre plates and incubated overnight at 37° C. These cultures are used as inoculum for expression cultures in 200 μL of 2×YT supplemented with ampicillin. When the optical densities at 600 nm of the cultures reach approximately 1.0, the expression of variants out of pGC is induced with addition of IPTG to 0.5-1 mM and incubation for 16 h at 20-22° C. The culture supernatants are then harvested for ELISA binding to RANKL and TRAIL coated overnight on well surfaces of microtitre plates. The surfaces are blocked with 0.5% casein for 2 h. Supernatants are filtered using microtitre plates fitted with 100 kD molecular weight cut-off (MWCO) membranes to remove higher molecular weight species and aggregates which helps reduce background signal in the ELISA. These filtered supernatants are applied to the antigen-coated and blocked wells. Detection of bound OVPs is achieved using mouse anti-FLAG antibody, then goat anti-mouse-peroxidase conjugate (BioRad). TMB (KPL) is used as peroxidase substrate with the binding signal measured by reading absorbance at 450 nm. Washes in between steps are done 3 times with PBS/0.05% Tween, then 3 times with PBS and dilutions are made in 0.25% casein. This first crude screen was assessed, with the most promising clones (based on RANKL-binding signal being retained at or close to the level of wild type OPG and TRAIL-binding signal being substantially reduced) selected for a secondary screen.

The secondary screen involves expressing selected clones in 10 ml cultures with an induction period of 3 h at 20-22° C. The periplasmic extracts from these cells are harvested, filtered as above, and then tested at a range of dilutions (generally from 1:2 to 1:32) by ELISA as above. The best of these proteins were chosen for large-scale expression and purification (0.5-2 L) as described above for OPG wild type. The purified proteins are quantitated by determination of extinction coefficients due to Trp and Tyr residues at $A_{280nm}$. The OVPs were then tested at equivalent concentrations in comparison to OPG wild type protein by ELISA as described above. The proteins were tested for binding in a doubling dilution series generally from a concentration of 0.5 μM to 0.031 μM. Most of the proteins which are in monomer format show retention of RANKL-binding at or close to that of OPG wild type, and substantial reduction in TRAIL-binding signal. An example of results from such an ELISA is shown in FIG. 2. Variants with the required profile of binding properties were produced from all selection strategies.

EXAMPLE 6

Repeat Ribosome Display and Selection Processes

Subsequent rounds of ribosome display and selection were undertaken to further improve some of the best candidate OVPs. To achieve this, genes for these OVPs were cloned into the pEGX vector and mutagenesis and display carried out as described above with the molar amounts of the soluble antigens used in selection altered to force selection pressure towards further reduction of TRAIL binding and maintenance of RANKL binding. Screening for the best variants was undertaken as described above with further mutants isolated with apparent improvements in the desired properties. The sequences of the best ribosome display-selected OVPs from all rounds of selection are shown in FIG. 3. Mutations at aa 115 within the Cys107-Cys118 loop were observed in many of the selected variants, as were several mutations in amino acids nearby in the area encompassing aas 102-130. This suggests that this region, and aa 115 in particular, is important for TRAIL binding and that some changes can be tolerated here without loss of RANKL binding.

EXAMPLE 7

Site Directed Mutagenesis

The locations of mutations pinpointed by ribosome display selection shown to be beneficial for altering the specificity of OPG were investigated further by employing site-directed mutagenesis at these positions. Additional amino acid changes were sampled at residues 115, 122, and 128 and the L40S mutation was combined with some of the mutations at these positions. Forward and reverse primers were designed that encoded the particular mutant residue, allowing PCR amplification of front and back fragments of the mutant OVP gene with complementary overhangs regions. PCR was used to join the two DNA segments together by priming off each other for an initial 10 cycles without primers, and then 30 cycles with flanking 5' and 3' primers for amplification of the full mutant gene with restriction sites for cloning.

A mammalian expression system was employed to allow for production of higher levels of the more biologically relevant stable dimeric form of the proteins for further ELISA and cell-based assays. The site-directed mutants and the best ribosome display-selected candidate OVP(1-194) genes (residues 1-21 constitute the signal peptide) were cloned into the mammalian expression vector pAPEX-3.Fc. This allows expression of the OVPs as fusions with a human Fc domain to form stable dimers. A C-terminal FLAG tag is also added. HEK 293 EBNA cells are used for expression. These adherent cells are passaged in DMEM media supplemented with 2 mM Glutamax (Invitrogen), 10% bovine calf serum, and 200 µg/mL geneticin and incubated at 37° C. in 5% $CO_2$. For transient transfection using lipofectamine (Invitrogen), near-confluent cells are harvested and $5\times10^6$ cells are used to seed a 10 cm tissue culture dish to a volume of 10 mL. The cells are allowed to adhere and grow for 24 h. 24 mg of pAPEX-3.Fc plasmid DNA harbouring the OVP of interest is mixed with 1.5 mL of DMEM. 60 ul lipofectamine is diluted in 1.5 mL DMEM and incubated for 5 mins at room temperature. The diluted DNA and lipofectamine are mixed, incubated for 20 min at room temperature, and then added dropwise to the culture dish. After overnight growth total cells from one dish are harvested and used to seed a T175 dish in 25-30 mL. Once cells have reached near-confluence (1-2 days) the serum-containing DMEM is replaced with 25-30 mL of Ex-cell 293T serum-free media (JRH Biosciences) supplemented with 4 mM Glutamax. After 3-4 days the media is collected, centrifuged, and filtered through a 0.22 µm syringe filter.

For purification of proteins secreted into the media the supernatants are applied to 1 mL of protein A (Sigma) resin equilibrated with PBS. Proteins bound to the protein A via their Fc portion are eluted with 0.1 M Gly, pH 3 and this is monitored at $A_{280nm}$. The eluate is neutralized by immediate dialysis against PBS. Dialysed protein is concentrated to 0.5 mL and subjected to gel filtration chromatography using a Superdex 200 column. The dominant peak corresponding to the OVP-Fc dimer is collected and identity confirmed by Western blot using anti-FLAG antibody and N-terminal sequencing which reveals OPG with signal peptide having been processed. Ion-exchange chromatography of gel filtration-purified OVP elutes one protein peak, suggesting homogeneity.

EXAMPLE 8

Screening Site-Directed OVP Mutants

Figure 4A:
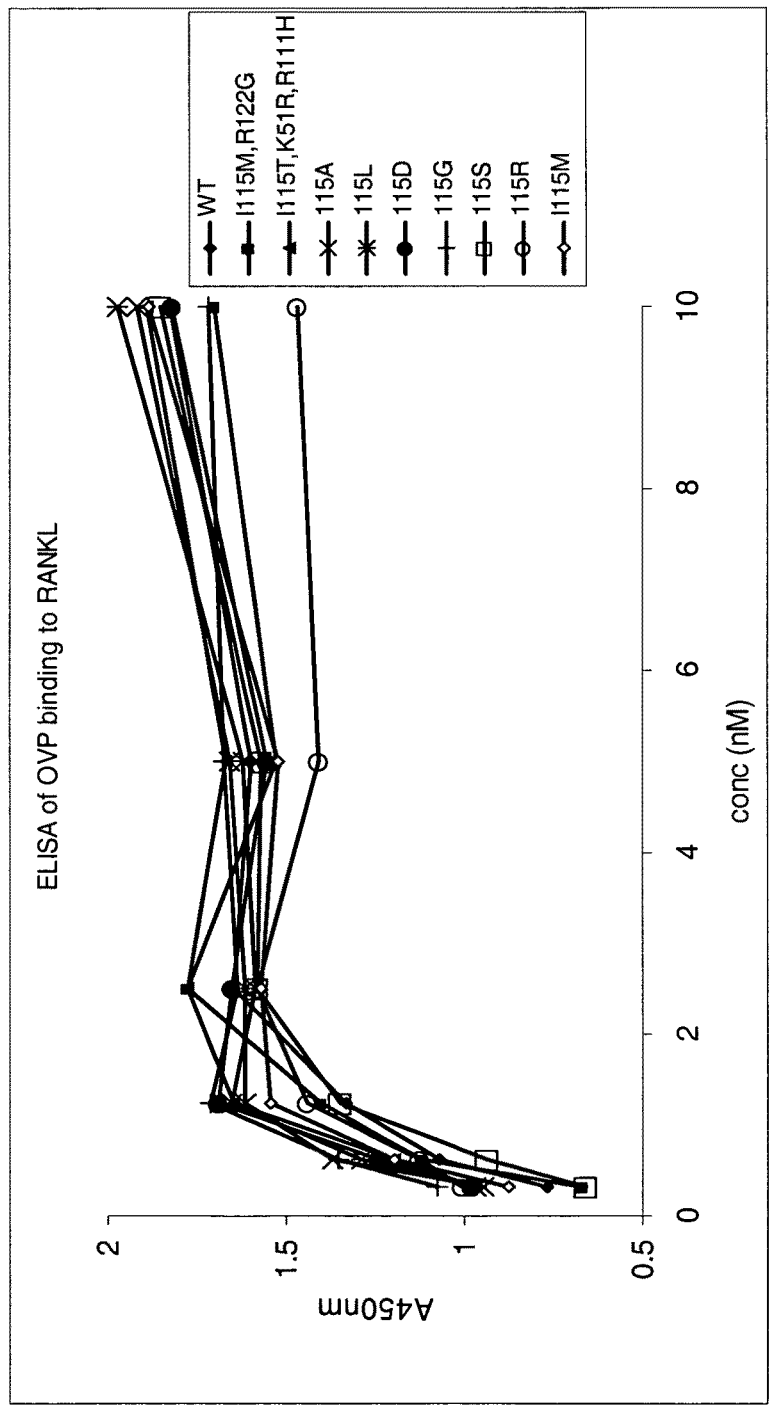
FIG. 4: ELISA of purified mammalian-expressed OVPs binding to RANKL (A) and TRAIL (B). These studies were carried out using dimeric Fc-linked OPG or OVP 22-194.
Figure 4B:
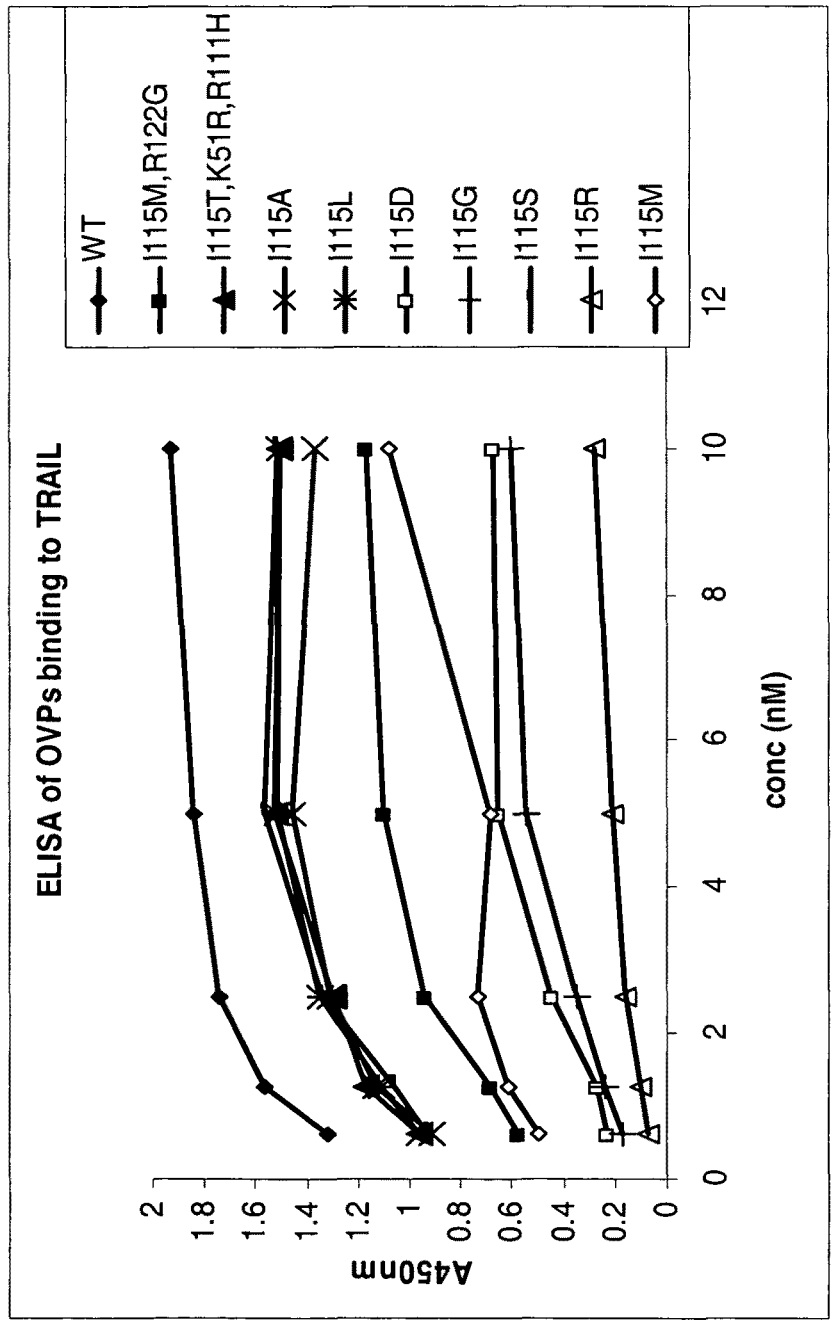

Purified mammalian-expressed OVP proteins are tested for binding to RANKL and TRAIL by ELISA. Wells are coated with RANKL at 5 µg/mL or TRAIL at 10 µg/mL in PBS O/N at 4° C., rinsed with PBS, blocked with 0.5% casein in PBS at room temp for 2 h, then rinsed again with PBS. Concentrations of OVPs to be tested are normalised to around 10 nM and then 50 µL applied to the antigen-coated wells in serial doubling dilutions over 6-7 wells for 1 h. All dilutions are made in 0.25% casein. All washes in between binding incubations are 3 times in PBS/0.05% Tween, then 3 times with PBS. Detection of bound OVPs is achieved with incubation of 50 µL anti-FLAG at 1.2 mg/mL for 20 min then 50 µl goat anti-mouse-peroxidase conjugate (BioRad) at 1:1500 for 20 min. TMB is used as enzyme substrate and then binding signal is measured at $A_{450nm}$. All OVPs or OPG wt are tested in the C-terminal Fc-linked format. An example of results from such an ELISA comparing binding of several OVPs to the OPG(22-194) wild type is shown in FIGS. 4A and 4B. The data shows that OPG(22-194) wt binds to both RANKL and TRAIL and that most OVPs maintain RANKL binding at or close to the level of the wild type protein. All the OVPs tested here show at least some reduction of binding to TRAIL compared to wt, with the ribosome display selected 1R17 (I115M), and site-directed mutants at position 115-115D, 115G, and 115R, showing very low levels of TRAIL binding. To enable approximate comparisons of relative binding of OVPs in ELISA, $EC_{50}$ values from the data are summarised in Table 1. $EC_{50}$ values were estimated by plotting binding responses against OVP dose on a logarithmic scale, with extrapolations made when the data does not reach the EC50 range. Some OVPs showed slight increase in binding to RANKL while in some RANKL binding was reduced by up to 3 fold.

EXAMPLE 9

Figure 5A:
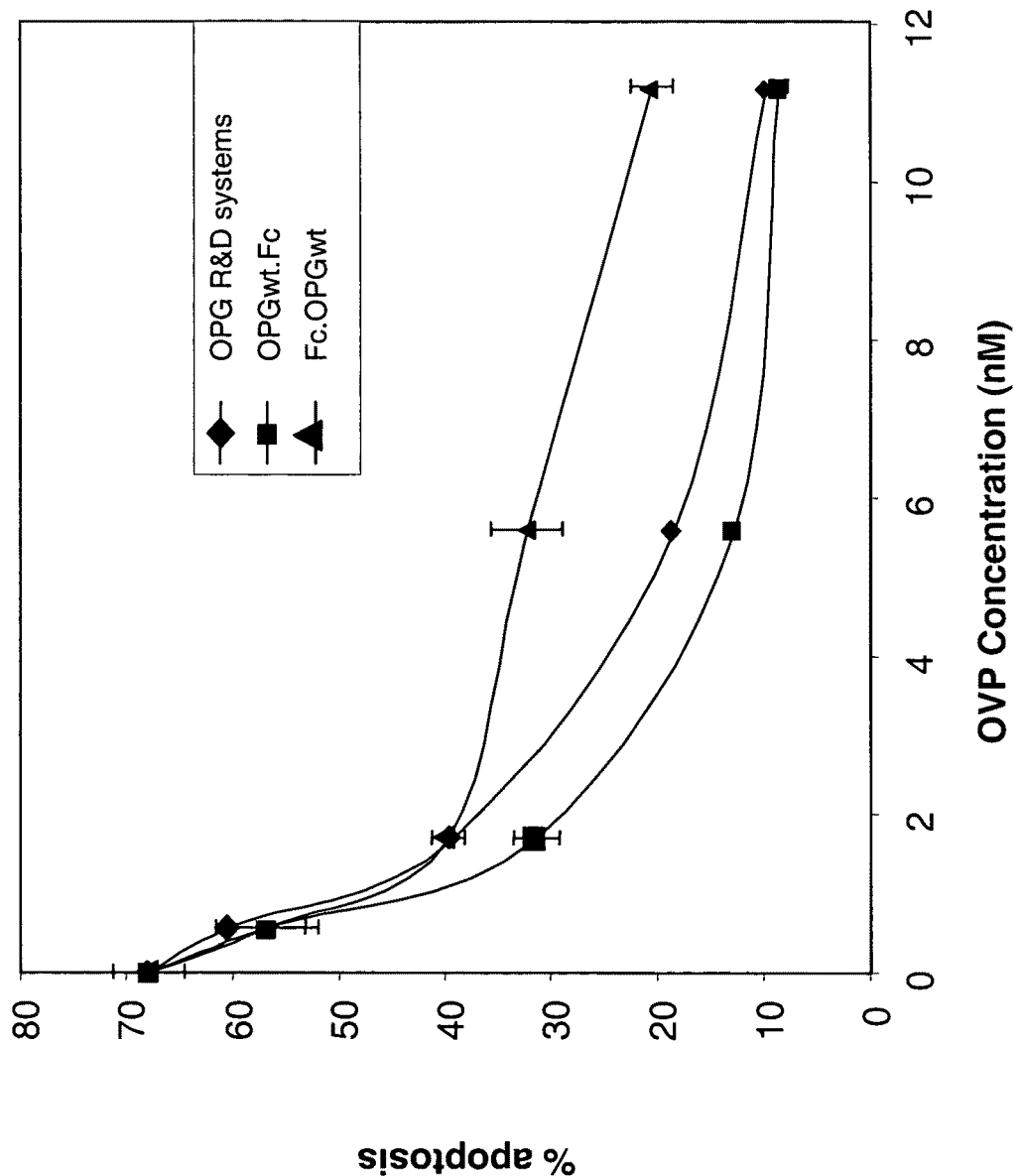
FIG. 5: (A) Inhibition of TRAIL-induced apoptosis in HCT116 cells by OPG wild type proteins. (B) Inhibition of TRAIL-induced apoptosis in HCT116 cells by OVPs.
Figure 5B:
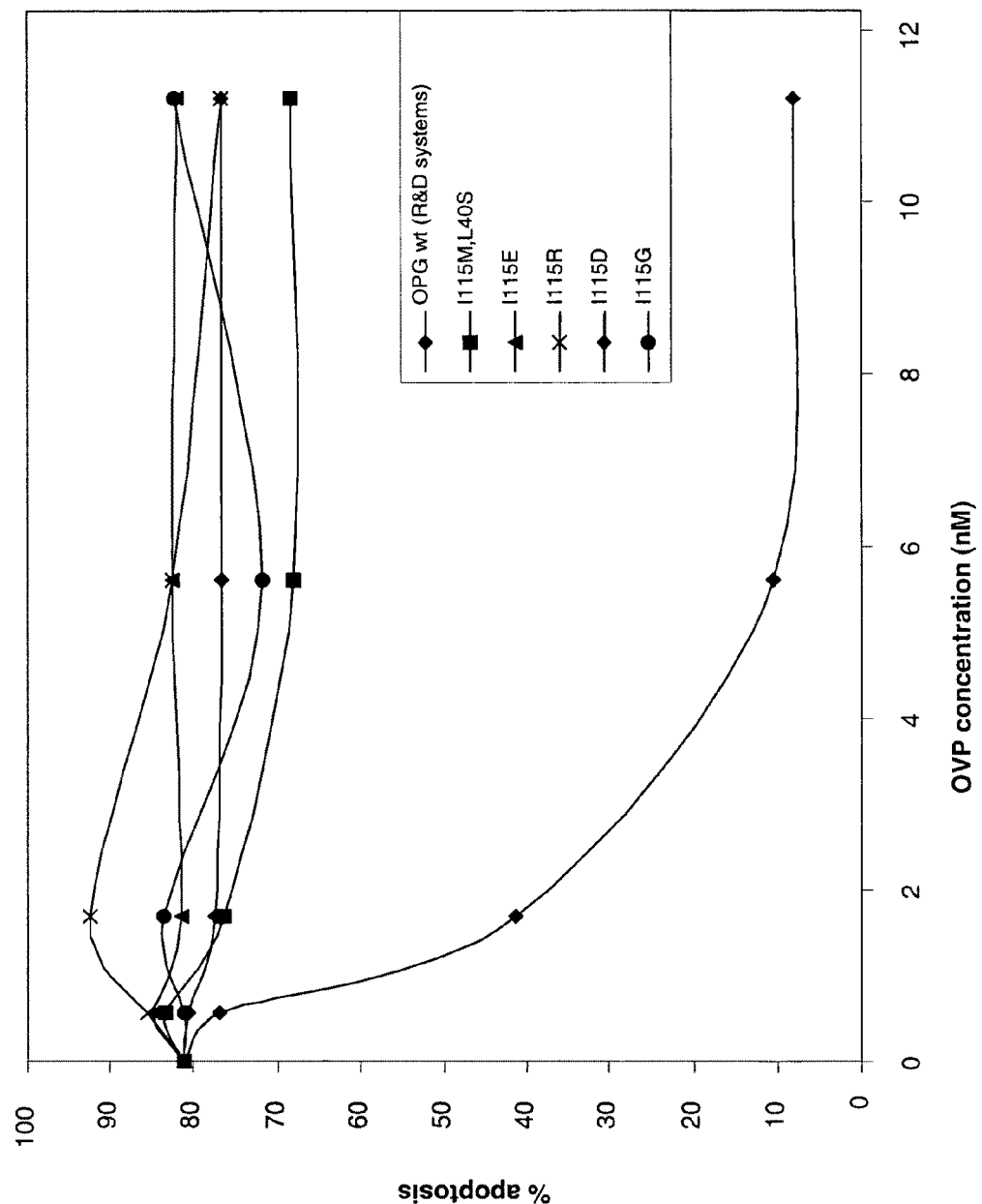

Biological Testing of OVPs in an Assay of TRAIL-Induced Apoptosis of HCT116 Cells The reduction of TRAIL-binding activity of OVPs observed in ELISA is further tested in an assay of TRAIL-induced apoptosis of HCT116 cells in the presence of these OVPs. These cells are cultured in DMEM containing 10% foetal calf serum (FCS) and 1% penicillin-streptomycin at 37° C. in 5% $CO_2$. HCT116 cells are plated in 12 well plates at $7.5\times10^4$ cells/well in 1 ml DMEM+FCS and allowed to attach and grow for 24 hours. Growth medium is then removed and replaced with 500 µL fresh medium for 1 hour at 37° C. OVPs or recombinant human OPG.Fc (R&D Systems) are added at 0.56, 1.69, 5.6 and 11.2 nM and the cells incubated a further 15 minutes at 37° C. before the addition of recombinant human TRAIL (R&D Systems) to 10 ng/ml (0.53 nM). The cells are then incubated for 16 hours at 37° C. before being harvested to score the percentage of apoptotic cells in each well. The maximum dose of OVP was tested in the absence of TRAIL for toxicity to cells. All cells (attached and floating) are harvested and resuspended in 20 μL of 1 mg/ml propidium iodide (PI), 0.1% Triton X-100, 0.1% sodium acetate in PBS. Apoptosis is scored by assessing nuclear morphology by fluorescence microscopy following PI staining with a cell scored as apoptotic if it displays one or more of the following: nuclear margination, chromatin condensation, or formation of apoptotic bodies. To avoid bias, samples are scored without knowing the treatment given to the sample. Examples of such an assay are shown in FIGS. 5A and 5B. The effect of wild type OPG proteins is shown in FIG. 5A where the proportion of cells exhibiting TRAIL-induced apoptosis is reduced from greater about 70% to under 10% at an OPG dose of 5.6 nM. The OPG(22-194).Fc appears to be similarly effective to the full-length OPG.Fc (R&D systems) molecule while an N-terminally linked-Fc version of the wild type protein is a little less effective. All the OVPs shown in FIG. 5B have little or no ability to inhibit TRAIL-induced apoptosis. Even at a dose four-fold higher than shown here there appears to be negligible TRAIL blocking activity with these selected OVPs.

EXAMPLE 10

Figure 6A:
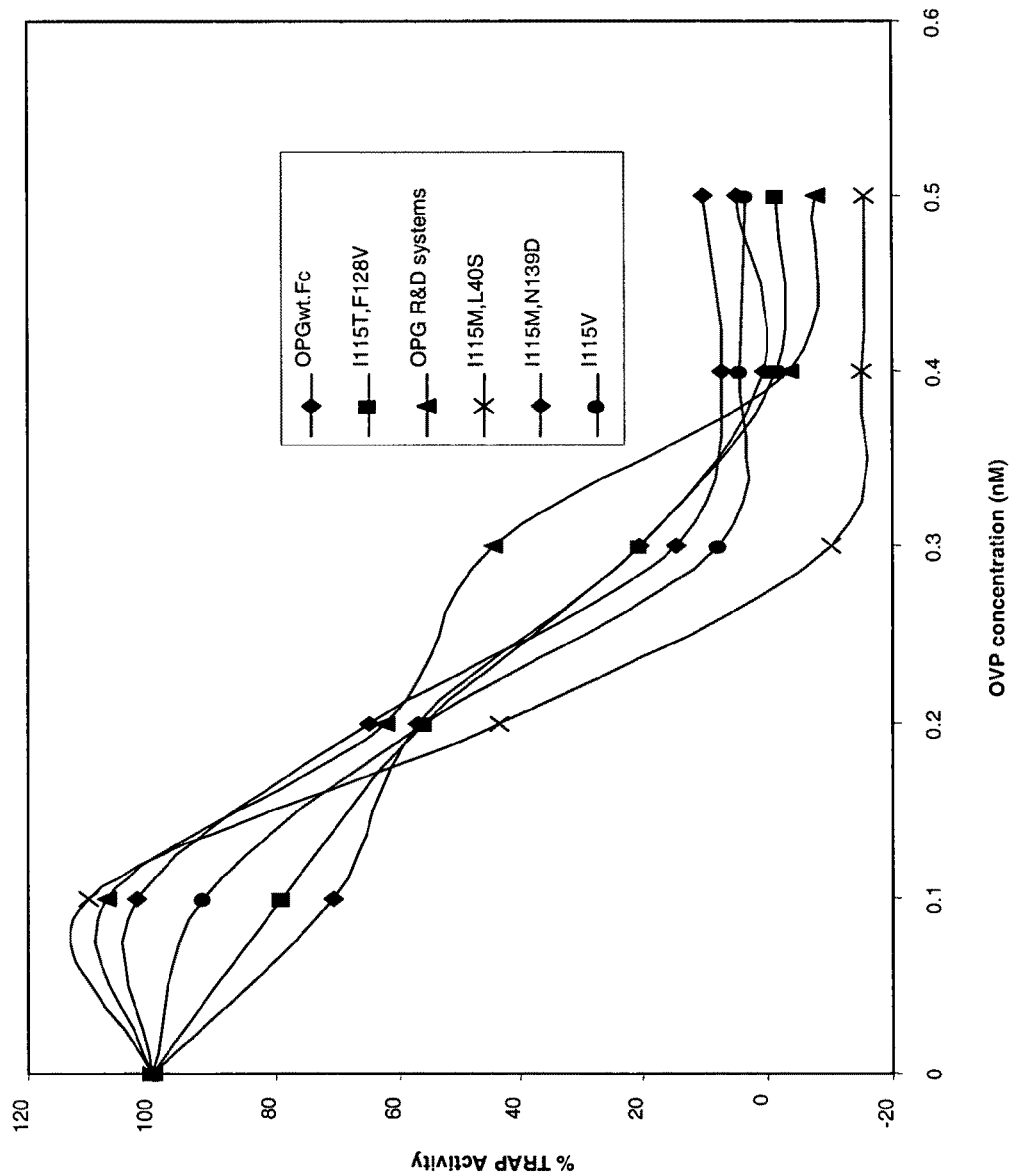
FIG. 6: (A) OPG wild type inhibition of RANKL-mediated Osteoclastic Activation of RAW264.7 cells. (B) OVP inhibition of RANKL-mediated Osteoclastic Activation of RAW264.7 cells.
Figure 6B:
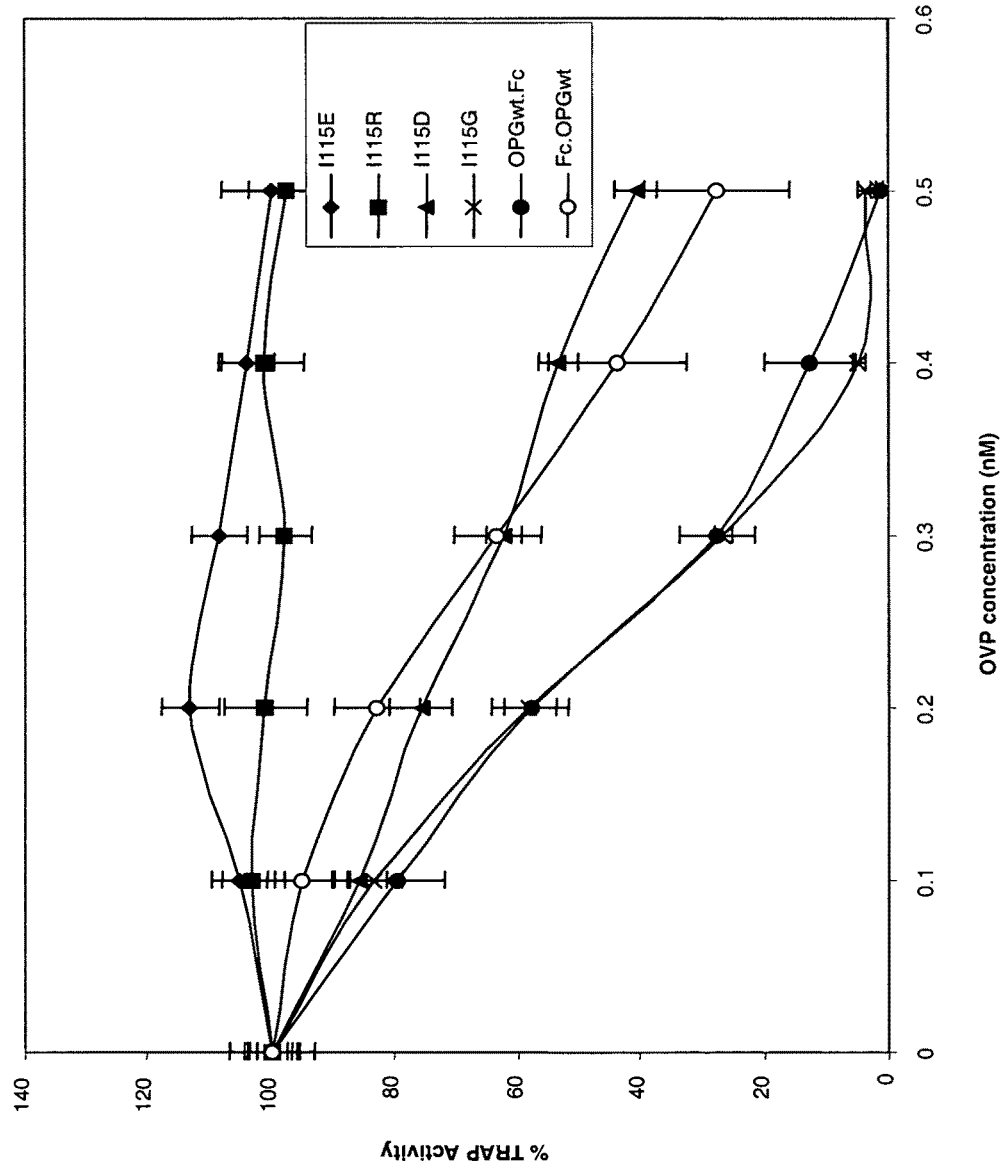

Biological Testing of OVPs in an Assay of RANKL-Mediated Differentiation of RAW264.7 Cells The murine leukaemia virus-induced tumour monocyte cell line RAW264.7 differentiates into osteoclasts under RANKL stimulation. To further test the ability of the OVPs to bind RANKL and block its biological effects mediated through binding to RANK, the RANKL-mediated differentiation of RAW264.7 cells in the presence of OVPs was assayed. RAW264.7 cells are cultured in DMEM containing 5% FCS and 1% penicillin-streptomycin at 37° C. in 5% CO2. RAW264.7 cells ($3\times10^3$ cells/well) are seeded into 96-well plates, in 100 μL DMEM and 5% FCS, and allowed to grow for 24 hours. An additional 100 μL of medium containing 15 ng/mL (0.75 nM) human RANKL (Roche) and OVPs from 0 to 0.5 nM is added to each well and the cells incubated a further 3 days. Osteoclast formation is evaluated by measuring tartrate-resistant acid phosphatase (TRAP) activity. The cells are fixed, dried, and 100 μL 50 mM citrate buffer pH 4.6, 10 mM tartrate, 1 mg/mL p-nitrophenylphosphate is added to measure TRAP activity. After incubation for 30 min, the reactions are stopped and absorbance measured at 405 nm. Such an assay is shown in FIG. 6A. At a dose of 0.4 nM, all of the OVPs shown are able to totally block the osteoclastic differentiation of RAW264.7 cells induced by 0.75 nM RANKL. FIG. 6B also shows such an assay involving OVPs generated by site-directed mutagenesis at aa115. Over this narrow range of low doses we can see a discrimination of RANKL-binding activities despite these proteins all showing substantial loss of the ability to inhibit TRAIL-induced apoptosis (FIG. 5B). It should be noted that some variants showed activity in this assay equivalent to or better than that of OPG. On the other hand, some variants that showed a relatively modest reduction in binding to RANKL (Table 1) showed significantly decreased ability to block RANKL mediated osteoclast activation.

EXAMPLE 11

Biological Testing of OVPs in a Giant Cell Tumour Osteoclast Resorption Assay

Figure 7:
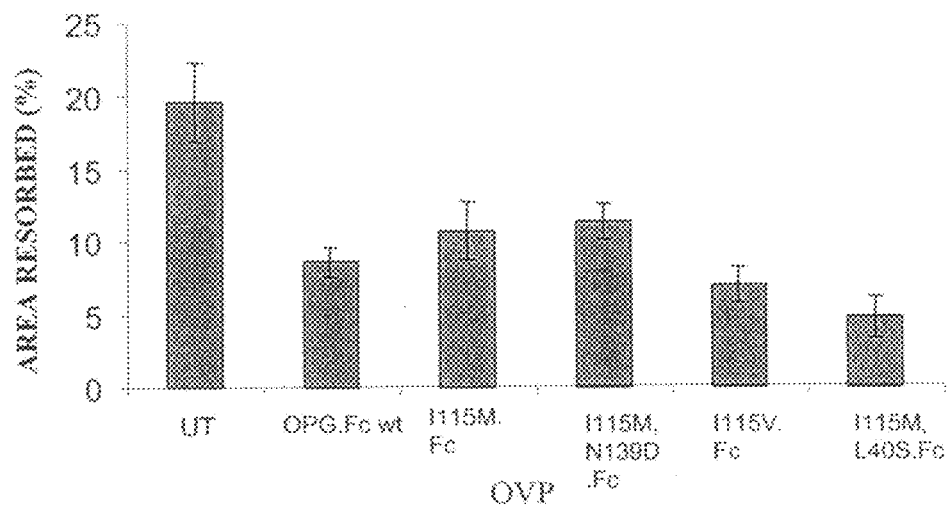
FIG. 7: OVP inhibition of RANKL-induced osteoclast mediated resorption. All OVPs used at 1 nM. UT—untreated with OVP

A giant cell tumour osteoclast resorption assay was also used as a means of measuring the biological effect of OVPs binding to RANKL. This is an assay (Atkins et al., Bone 28:370-37 (2001)) for RANKL-mediated osteoclastogenesis by measuring the level of resorption pit formation in dentine slices. The assay can be used to show the OPG-mediated inhibition of this effect. Both the number of resorption pits and area of resorption can be quantitated. An example of this assay testing several OVPs is shown in FIG. 7. All constructs showed inhibition, with the OPG wt at about 55% inhibition and the best OVP, R23 (I115M, L40S), showing 75% inhibition.

EXAMPLE 12

Conclusions from Biological Testing of OVPs

Figure 8:
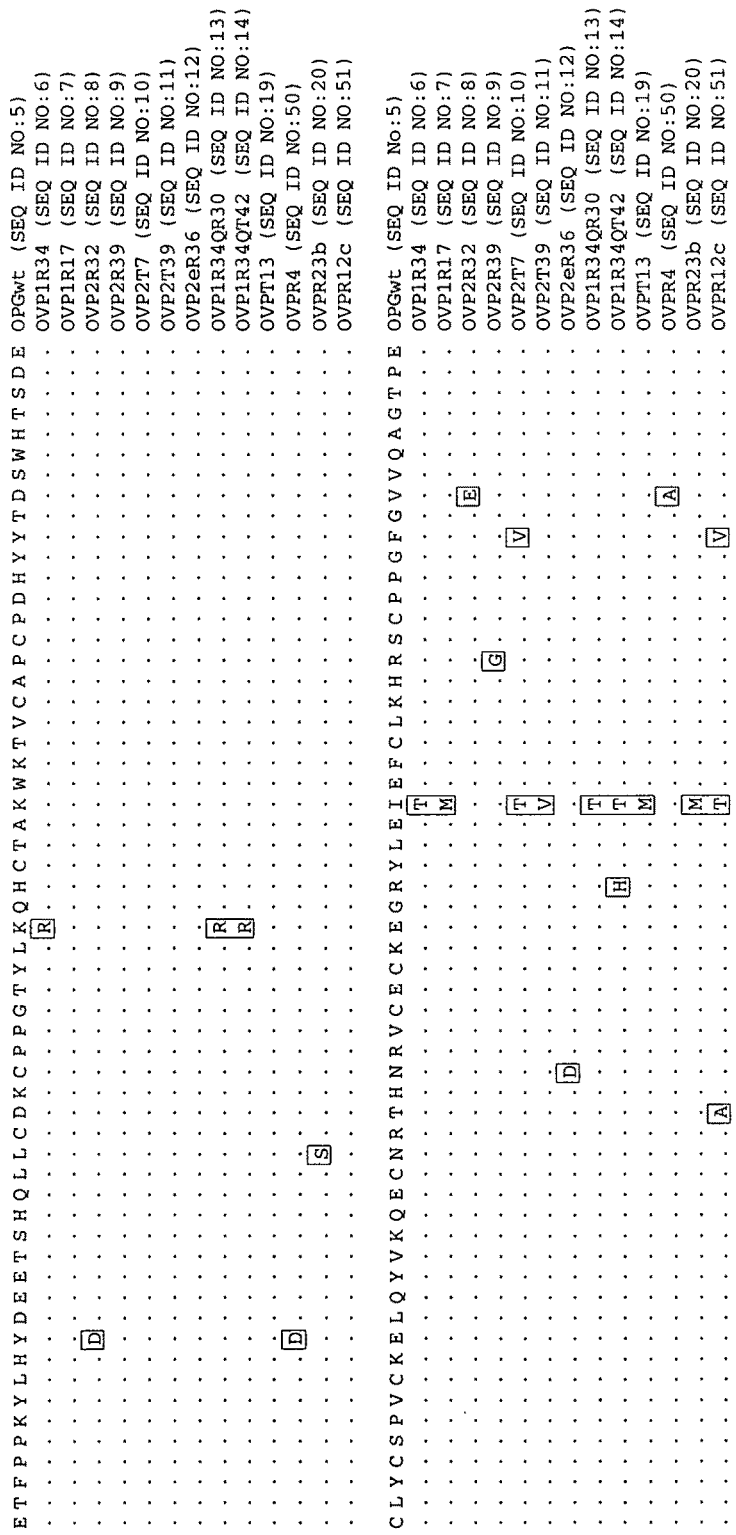
FIG. 8: Alignments of human OPG wild-type and preferred OVP amino acid sequences.
Figure 9:
FIG. 9: Structural model of OPG bound to mouse RANKL (pdb file 1JTZ). The RANKL trimer is visualized as the upper light gray ribbon diagram, OPG as dark gray ribbon diagram. OPG residues with at least one atom within 5 Angstrom of RANKL are highlighted as spacefilling spheres. Light spheres represent potential contact residues of OPG to RANKL in the N-terminal receptor domain (residues 42 to 91 of OPG, with specific contact residues scored as 42, 43, 49, 50, 52, 53, 69, 71-82, 85-91), dark spheres show the C-terminal receptor domain (OPG residues 105 to 130 with specific contact residues scored as 105, 106, 107, 108, 110-130).
Figure 10:
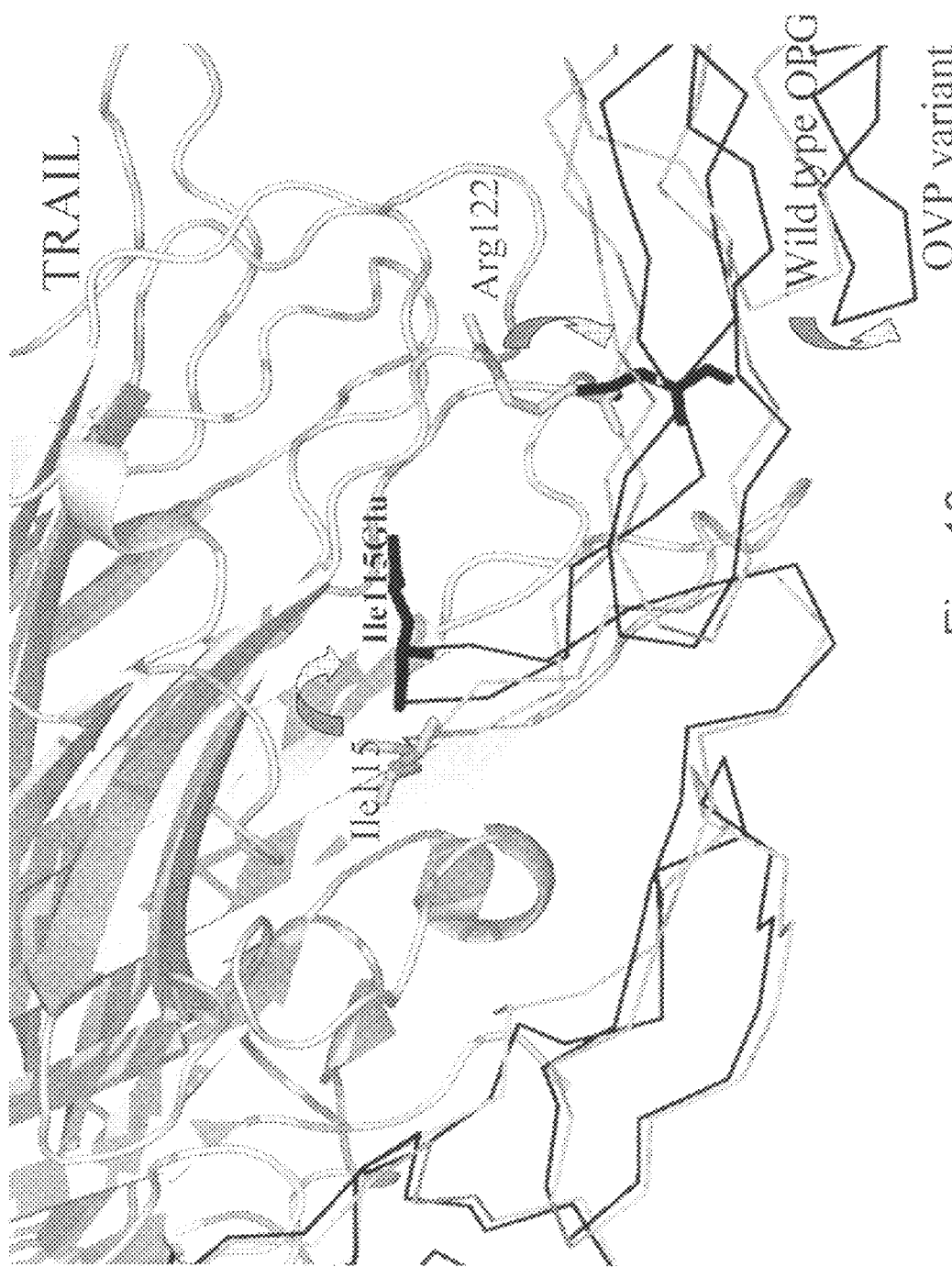
FIG. 10: Partial view of modelled OPG in contact with TRAIL focusing on the second TNF receptor domain. In the upper half TRAIL is shown as ribbon diagram. OPG is depicted as alpha carbon trace in light grey. In black, an OPG variant is aligned with OPG, featuring mutation of Ile 115 to Glu. Side chains for residues 115 and 122 are shown as stick figures. The modelling of the OVP suggests that mutation of residue 115 results in an altered conformation of the 107-118 loop, with realigned contacts in the interface. The conformational change may alter additional contacts, as highlighted by the shift of the side chain of residue 122, potentially abolishing contacts in the region of residues 120-130. These contacts appear more crucial for TRAIL than for RANKL binding. This would be consistent with the nearly complete abolishment of TRAIL binding seen for this mutant in our assays.
Figure 11:
FIG. 11: Model predicting the association between OPG (bottom) and TRAIL (top as ribbon diagram). Residues 102-130 are shown in space-filling form. According to this model, the loop containing residue 115 of OPG (long arrow), and residues C-terminal to this (to the right of the 115 loop) make multiple contacts with TRAIL (short arrow). The protruding loop 195-202 of TRAIL (short arrow) appears to allow additional or more extensive contacts with OPG than are possible for RANKL in particular with OPG residues 120-130 (compare to FIG. 12). This confirms the region as an area where mutations are likely to alter TRAIL binding with the potential for unaltered RANKL binding.
Figure 12:
FIG. 12: Model predicting the association between OPG (bottom) and RANKL (top as ribbon diagram), using the mouse RANKL structure, aligned to modelled OPG-TRAIL complex. Residues 102-130 of OPG are shown in spacefilling form. The loop containing residue 115 long arrow) points towards and contacts RANKL, but residues C-terminal to this area (to the right of this loop) appear to have few contacts with RANKL (short arrow-RANKL residues 225-233, which corresponds to the protruding loop 195-202 in TRAIL of FIG. 11). This distinguishes the contact of OPG with RANKL from that of TRAIL shown in the previous diagram.

The sequences of selected OVPs isolated by ribosome and display selection are shown in FIG. 8. Results of binding studies conducted on these OVPs and additional OVPs generated by site directed mutagenesis are shown in Table 1.

It is clear from the data shown in Table 1 that substitutions at residue position 115 have a major impact on the ability of the OVP to bind to TRAIL. In particular, substitution of residues such as Met, Gly, Asn, Asp and Glu at this position lead to a substantial reduction in binding to TRAIL without significantly affecting binding to RANKL. Further, none of the OVPs generated with these substitutions showed any activity in an assay of TRAIL-induced apoptosis of tumour cells.

Mutations at residue 122 also have an impact on the ability of OVPs to bind to TRAIL. For example, double mutants 1I115M, R122N and I115M, R122E showed substantially reduced binding affinity for TRAIL.

Mutations at residue 128 also have an impact on the ability of OVPs to bind to TRAIL. For example, double mutants 1I115M, F128L and I115M, F128I showed substantially reduced binding affinity for TRAIL.

The double mutant I115M, L40S resulted in a 75% inhibition of RANKL-mediated osteoclasogenesis which highlights the importance of mutations at residue 40.

A summary of biological activity of selected OVPs in cell-based assays is provided in Table 2.

EXAMPLE 13

OPG/OPV Three Dimensional Structure Modelling

OPG is classified as a member of the TNF-receptor superfamily of proteins. Members most notably feature multiple repeats of a approximately 40 amino acids, cysteine-rich domains, that are involved in ligand binding. Known ligands include the structurally homologous TRAIL and RANKL proteins.

No three dimensional structure has been published for OPG alone or in combination with either of its ligands RANKL or TRAIL. A structural model was therefore established of the two cysteine-rich domains in the amino terminal fragment of OPG, in an attempt to examine the likely effect of mutations contained in preferred OVPs.

From a BLAST search of the Brookhaven protein structure database (PDB), three close homologues of TNF-receptor related proteins were selected for which three-dimensional structures had been determined, namely polypeptides in pdb files 1 SG1 (Receptor-Ligand Complex between Nerve Growth Factor and the Common Neurotrophin Receptor p75), and Death Receptor 5 structures from the files 1D4V and 1DU3. In addition, a structure from file 1D0G was added. The TNF-receptor superfamily member DR5 (a TRAIL receptor protein) is represented in this structure complexed to a trimer of TRAIL that was exploited for the design of models for the OPG ligand complex. The modelling was performed using the module Modeller within the InsightII software package (Molecular Simulations Inc.). The structure of 1SG1 X chain was furthermore divided into an N-terminal and a C-terminal domain and the two domains were separately aligned with the remaining templates, as both domains had shown homology to OPG. Compared to the other three templates there appeared to be a hinge region in the protein allowing the C-terminal domain to be displaced. Fifty models were generated for the wild type OPG fragment used as the starting point for selection experiments as well as for a number of the selected OVP sequences. The models were ranked according to scores from Modeller, and the top 10 ranked models were aligned to DR5 in the 1D0G structure. The receptor contact regions of the TRAIL component of this structure, was in turn used to model a possible contact structure of receptors on RANKL, using the determined structure of mouse RANKL (pdb file 1JTZ). This process allowed a comparison of modelled OPG when binding TRAIL and RANKL structures. The resulting models of the complex of OPG, in its modelled structure, with TRAIL or RANKL respectively, were examined for steric clashes and potential binding interactions.

Our models of the OPG protein suggested that binding of both RANKL and TRAIL could occur with the extensive interface found in similar TNF-receptor-Ligand interactions (Hymowitz et al., Mol. Cell 4:563-571 (1999); He et al., Science 304: 870-875 (2004). As predicted from our modelling, two TNF-receptor like domains of OPG appear to be involved in binding both RANKL and TRAIL (see FIGS. 9 to 12), the N-terminal domain having contacts within the region of residues 42 to 92 and the C-terminal domain within the region of residues 107 to 154. Two subregions were detected which appeared particularly significant—107-118 and 120-142. The N-terminal domain contacts with OPG appear similar between RANKL and TRAIL, therefore mutations in this region would be more likely result in effects on both binding interactions. This is consistent with the results of the selection experiments reported herein, as this region was not one where frequent mutation was found in OVPs selected for reduced binding to TRAIL but not to RANKL.

There appears to be a hinge around the disulfide bond between residues 124 to 142, allowing the C-terminal domain to either bend away from the ligand, thereby limiting interactions or bend towards the ligand to form more interactions. There are furthermore differences in conformation between the two ligands examined, TRAIL and RANKL. Residues Glu195 to Asn202 in TRAIL, in particular Asn199, Thr200 and Lys201 protrude as a loop region towards the OPG binding site, potentially contacting OPG within the region of residues Leu119 to Arg143 in OPG, with the most likely contacted residues Lys120, His121, Arg122, Cys124, Pro125, Pro126, Gly127, Phe128, Cys141, Lys142.

However, the precise positioning of this region appears to be additionally guided by contacts within the protruding loop N-terminal to the hinge region, which is enclosed between Cys107 and Cys118. Within this loop, Glu116 and Phe117 appear capable of forming sets of favourable interactions in at least two orientations. Mutations in the neighbouring residue Ile115, for example I115G or I115E, appear to bias for one orientation, which could translate to a more open position and thereby weaken the interaction of C-terminal contacts to the 195-202 loop of TRAIL while maintaining the RANKL interaction. Some changes at residue 115, however, were found in these studies to disrupt binding to RANKL as well as to TRAIL. These changes were ones where the substituted amino acid had a larger side chain in combination with a positive or negative charge. This suggests that residue 115 is also involved in contacting RANKL or that unfavourable changes to this residue disrupt important contacts made by neighbouring residues such as 116.

Modelling of changes within the region 120-142 suggest that alterations in any one of a number of residues in this region might influence binding to TRAIL specifically, and a number of such changes have been detected amongst the OVPs examined.

Within the N-terminal binding region, residues 42-92 of OPG form a broad contact region with both RANKL and TRAIL. Both ligand structures appear similar in this interface. Since this was not a region where mutations leading to loss of TRAIL binding were observed in the work described herein, we conclude that residues in this region may in reality contribute more weakly to TRAIL binding, or that mutations in this region affect binding to TRAIL and RANKL in parallel, so that changes in this area were not selected during our screening strategy. Nonetheless, subtle conformational changes due to mutations in this or a nearby area may possibly alter the properties of the molecule favourably for its RANKL-mediated effects, as it has been suggested above for a conformational shift due to mutation of residue 115. Of particular interest is a change at residue 40 identified among OVPs examined. Since this residue lies adjacent to this contact region, it is likely that changes in nearby residues may subtly influence the shape of this loop, thereby preferentially biasing binding towards RANKL at the expense of TRAIL attachment. It is likely that such subtle shifts in shape may be achieved by mutation in other OPG residues that can affect folding of this domain.

All references cited above are incorporated herein in their entirety by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

TABLE 1

| | OVP binding studies | |
|---|---|---|
| Variants | RANKL fold change cf wt | TRAIL fold change cf wt |
| I115V | 1.5 | (4) |
| I115L | 1.75 | (4.3) |
| I115M | 1.2 | (25) |
| I115W | (1.4) | (5) |

TABLE 1-continued

OVP binding studies

| Variants | RANKL fold change cf wt | TRAIL fold change cf wt |
|---|---|---|
| I115A | 2.25 | (2.5) |
| I115G | 2.1 | (>125#) |
| I115N | (1.1) | (390#) |
| I115S | (1.4) | (3.1) |
| I115R | (2.3) | (50#) |
| I115K | (60) | No binding |
| I115Y | 1.1 | (3) |
| I115D | 1.5 | (>125) |
| I115E | (2.25) | (>250) |
| N102D | 1.1 | (1) |
| I115M, L40S | 1.1 | (>250) |
| I115M, N139D | (1.75) | (60) |
| I115T, K51R | (1.75) | (0.8) |
| I115M plus: | | |
| R122G | 1 | (12.5) |
| R122N | (1.1) | (>250) |
| R122Q | 2.5 | (3) |
| R122S | 1.5 | (3.5) |
| R122D | (6) | (23) |
| R122E | (1.2) | (>250) |
| I115M plus: | | |
| F128L | 1.2 | (250#) |
| F128A | 1.2 | (2) |
| F128S | 1 | (50) |
| F128T | (3.3) | (7) |
| F128I | (2.1) | (250#) |
| I115T, K51R, R111H | 1.5 | (7.5) |
| I115T, K51R, S167G | 1.5 | (15) | by extrapolation
increase in binding = lower EC50;
( ) reduction in binding – higher EC50

TABLE 2

Summary of biological activity in cell-based assays

| OPG variant protein | TRAIL-induced apoptosis assay* | RAW cells assay | GCT resorption assay |
|---|---|---|---|
| OPG wt | +++++ | +++++ | +++ |
| OPG (R&D systems) | +++++ | ++++ | |
| I115T, K51R | +++ | +++++ | |
| I115M | ++ | +++ | ++ |
| I115M, N139D | ++/+++ | +++++ | ++ |
| I115T, K51R, S167G | +++ | +++++ | |
| I115T, F128V | ++ | +++++ | |
| I115V | ++++ | +++++ | +++ |
| I115M, L40S | ++ | +++++ | ++++ |
| I115D | + | ++++ | |
| I115G | + | +++++ | |
| I115R | – | ++ | |
| I115E | – | + | |

*– least ability to block TRAIL-induced apoptosis +++++ greatest ability to block TRAIL-induced apoptosis

The invention claimed is:

1. An osteoprotegerin (OPG) variant protein and conservative substitutions thereof, the variant protein consists of one to three modifications of the wild-type OPG, one of which is a modification at residue 122 when compared to wild-type OPG, wherein the OPG variant protein or conservative substitution thereof retains binding affinity for receptor activator of NFκB ligand (RANKL) but exhibits reduced binding affinity for TNF-related apoptosis inducing ligand (TRAIL) when compared to wild-type OPG.

2. An OPG variant protein as claimed in claim 1, which comprises at least one amino acid substitution at residue position 102, 111, 115, 128 or 130.

3. An OPG variant protein as claimed in claim 1, which comprises at least one modification within the loop structure comprising residues 107-118.

4. An OPG variant protein as claimed in claim 3, which comprises a modification at residue 115.

5. An OPG variant protein as claimed in claim 1, which exhibits a binding affinity for RANKL that is at least 80% that of wild type OPG.

6. An OPG variant protein as claimed in claim 1, which has an $EC_{50}$ (nM) for RANKL of less than 1 nM under ELISA assay conditions wherein the OPG variant protein and wild type OPG are each tested as a fusion with a human Fc domain.

7. An OPG variant protein as claimed in claim 1, which exhibits a binding affinity for TRAIL that is less than 20% that of wild type OPG.

8. An OPG variant protein as claimed in claim 1, which has an $EC_{50}$ (nM) for TRAIL of greater than 10 nM under ELISA assay conditions wherein the OPG variant protein and wild type OPG are each tested as a fusion with a human Fc domain.

9. An OPG variant protein as claimed in claim 1, wherein the OPG variant protein is conjugated to a polypeptide.

10. An OPG variant protein as claimed in claim 9, wherein the polypeptide is an immunoglobulin constant domain.

11. A dimer or multimer comprising at least two OPG variant proteins as claimed in claim 1.

12. An isolated polynucleotide encoding an OPG variant protein as claimed in claim 1.

13. A composition for inhibiting or reducing binding of RANK to RANKL, the composition comprising an OPG variant protein as claimed in claim 1, and one or more acceptable carriers.

14. An OPG variant protein as claimed in claim 1, which exhibits a binding affinity for RANKL that is at least 50% that of wild type OPG.

15. An OPG variant protein as claimed in claim 1, which exhibits a binding affinity for RANKL that is at least 60% that of wild type OPG.

16. An OPG variant protein as claimed in claim 1, which exhibits a binding affinity for RANKL that is at least 70% that of wild type OPG.

17. An OPG variant protein as claimed in claim 1, which exhibits a binding affinity for TRAIL that is less than 50% that of wild type OPG.

18. An OPG variant protein as claimed in claim 1, which exhibits a binding affinity for TRAIL that is less than 40% that of wild type OPG.

19. An OPG variant protein as claimed in claim 1, which exhibits a binding affinity for TRAIL that is less than 30% that of wild type OPG.

20. An OPG variant protein as claimed in claim 1, wherein the protein is a modified fragment of OPG comprising amino acids 22-194.

21. An OPG variant protein as claimed in claim 1, wherein the modifications are within the region encompassed by residues 102-130.

* * * * *